US005653939A

United States Patent [19]
Hollis et al.

[11] Patent Number: 5,653,939
[45] Date of Patent: Aug. 5, 1997

[54] OPTICAL AND ELECTRICAL METHODS AND APPARATUS FOR MOLECULE DETECTION

[75] Inventors: Mark A. Hollis, Concord; Daniel J. Ehrlich, Lexington; R. Allen Murphy, Boxboro; Bernard B. Kosicki, Acton; Dennis D. Rathman, Ashland; Chang-Lee Chen, Sudbury; Richard H. Mathews, Chelmsford; Barry E. Burke, Lexington, all of Mass.; Mitch D. Eggers, The Woodlands, Tex.; Michael E. Hogan, The Woodlands, Tex.; Rajender Singh Varma, The Woodlands, Tex.

[73] Assignees: Massachusetts Institute of Technology, Cambridge, Mass.; Houston Advanced Research Center, The Woodlands; Baylor College of Medicine, Houston, both of Tex.

[21] Appl. No.: 511,649

[22] Filed: Aug. 7, 1995

Related U.S. Application Data

[60] Division of Ser. No. 872,582, Apr. 23, 1992, which is a continuation-in-part of Ser. No. 794,036, Nov. 19, 1991, abandoned.

[51] Int. Cl.$^6$ .......................... G01N 15/06; G01N 27/02; C07K 1/00
[52] U.S. Cl. .............. 422/50; 422/68.1; 422/76; 422/82.01; 422/82.02; 422/82.05; 422/91.2; 204/456; 435/5; 435/6; 435/7.1; 435/7.9; 435/285.2; 436/149; 436/150; 436/806; 436/807; 530/300; 530/350; 530/333
[58] Field of Search .................. 435/6, 5, 91.1, 435/7.1–7.9, 288, 91.2; 536/25.3, 26.6, 24.3, 33; 422/50, 68.1, 76, 82.01, 82.02, 82.05, 186, 186.04, 197; 204/91, 182.8; 436/149, 150, 806, 807, 809, 518, 516, 527; 530/300, 350; 350/333, 334, 338

[56] References Cited

U.S. PATENT DOCUMENTS

| | | | |
|---|---|---|---|
| 4,054,646 | 10/1977 | Giaever | 424/12 |
| 4,072,576 | 2/1978 | Arwin | 395/103.5 R |
| 4,238,757 | 12/1980 | Schenck | 357/25 |
| 4,314,821 | 2/1982 | Rice | 23/230 |
| 4,571,543 | 2/1986 | Raymond et al. | 324/425 |
| 4,580,895 | 4/1986 | Patel | 356/39 |
| 4,728,882 | 3/1988 | Stanbro et al. | 324/61 |
| 4,760,105 | 7/1988 | Fuller et al. | 523/420 |
| 4,769,121 | 9/1988 | Newman | 204/403 |
| 4,777,019 | 10/1988 | Dandekar | 422/68 |
| 4,816,418 | 3/1989 | Mack et al. | 436/518 |
| 4,822,566 | 4/1989 | Newman | 422/86 |
| 4,908,112 | 3/1990 | Pace | 204/299 |
| 4,935,207 | 6/1990 | Stanbro et al. | 422/68.1 |
| 4,938,742 | 7/1990 | Smits | 604/67 |
| 4,963,245 | 10/1990 | Weetall | 204/403 |
| 5,047,213 | 9/1991 | Funlan et al. | 422/82.11 |
| 5,063,081 | 11/1991 | Cozette et al. | 427/2 |
| 5,064,754 | 11/1991 | Mills | 435/6 |
| 5,071,733 | 12/1991 | Uekita et al. | 430/326 |
| 5,075,077 | 12/1991 | Durley, III et al. | 422/56 |
| 5,082,627 | 1/1992 | Stanbro et al. | 422/82.01 |
| 5,096,807 | 3/1992 | Leaback | 435/6 |
| 5,143,854 | 9/1992 | Pirrung et al. | 436/518 |
| 5,156,810 | 10/1992 | Ribi et al. | 422/82.01 |
| 5,164,319 | 11/1992 | Hafeman et al. | 435/291 |
| 5,187,096 | 2/1993 | Giaever et al. | 435/291 |
| 5,194,133 | 3/1993 | Clark et al. | 204/299 |
| 5,200,051 | 4/1993 | Cozzette et al. | 204/403 |
| 5,202,231 | 4/1993 | Drmanac et al. | 435/6 |
| 5,221,605 | 6/1993 | Band et al. | 435/4 |
| 5,234,566 | 8/1993 | Osman et al. | 204/403 |
| 5,298,414 | 3/1994 | Bruce et al. | 435/26 |
| 5,310,686 | 5/1994 | Sawyers et al. | 436/518 |
| 5,313,264 | 5/1994 | Ivarsson et al. | 356/73 |
| 5,384,261 | 1/1995 | Winkler et al. | 436/518 |

FOREIGN PATENT DOCUMENTS

| | | | |
|---|---|---|---|
| 0295965 | 12/1988 | European Pat. Off. | |
| 0 376 611 A2 | 7/1990 | European Pat. Off. | G01N 27/26 |
| 0402917A3 | 12/1990 | European Pat. Off. | G01N 33/48 |
| 0347579 | 12/1989 | Germany | B01L 3/00 |
| 2202045 | 9/1988 | United Kingdom | G01N 21/64 |
| 87/03095 | 5/1987 | WIPO | G01N 33/566 |
| 88/08528 | 11/1988 | WIPO | G01N 21/00 |
| 88/09499 | 12/1988 | WIPO | G01N 27/22 |
| 89/10977 | 11/1989 | WIPO | C12Q 1/68 |
| 90/02327 | 3/1990 | WIPO | G01N 27/40 |
| WO90/03382 | 4/1990 | WIPO | C07H 21/00 |
| 90/05300 | 5/1990 | WIPO | G01N 27/48 |
| 9015070 | 12/1990 | WIPO | C07K 1/04 |
| WO90/15070 | 12/1990 | WIPO | C07K 1/04 |
| WO91/18117 | 11/1991 | WIPO | C12Q 1/68 |
| 92/04470 | 3/1992 | WIPO | C12Q 1/68 |
| WO92/10092 | 6/1992 | WIPO | A01N 1/02 |
| WO92/10587 | 6/1992 | WIPO | C12Q 1/68 |
| WO92/10588 | 6/1992 | WIPO | C12Q 1/68 |
| WO93/22678 | 11/1993 | WIPO | |
| WO95/12808 | 5/1995 | WIPO | |

OTHER PUBLICATIONS

Ekins et al., J. of Clinical Immunoassay, 13:169–181, 1996.
Pretty–Johns, et al., SPIE, 570:82–88, Aug. 22–23, 1985.
R.F. Taylor, Chap. 8, "Immobilized Antibody—and Receptor–Based Biosensors," *Protein Immobilization—Fundamentals and Applications*, ed R.F. Taylor, pp. 263–303 (1991).

(List continued on next page.)

*Primary Examiner*—W. Gary Jones
*Assistant Examiner*—Dianne Rees
*Attorney, Agent, or Firm*—Hamilton, Brook, Smith & Reynolds, P.C.

[57] ABSTRACT

A method and apparatus are disclosed for identifying molecular structures within a sample substance using a monolithic array of test sites formed on a substrate upon which the sample substance is applied. Each test site includes probes formed therein to bond with a predetermined target molecular structure or structures. A signal is applied to the test sites and certain electrical, mechanical and/or optical properties of the test sites are detected to determine which probes have bonded to an associated target molecular structure.

39 Claims, 13 Drawing Sheets

OTHER PUBLICATIONS

S.P.A. Fodor, et al., "Light-Directed, Spatially Addressable Parallel Chemical Synthesis," *Science*, vol. 251, pp. 767–773 (Feb. 1991).

Gronow, Chap. 20: Biosensors—"A Marriage of Biochemistry and Microelectronics", Biotechnology, The Science & The Business, Moses, Cape, pp. 355–370 (1991).

Khrapko, et al., "An Oligonucleotide Hybridization Approach to DNA Sequencing", *FEBS Letters* vol. 256, No. 1,2:118–122 (1989).

Khrapko, et al., "A Method for DNA Sequencing by Hybridization with Oligonucleotide Matrix", in *DNA Sequencing and Mapping*, vol. 1:375–388 (1991).

Suzuki, et al., "A 1024–Element High–Performance Silicon Tactile Imager," *IEEE IEDM* 88, pp. 674–677 (1988).

Sugiyama, et al., "Micro–Diaphragm Pressure Sensor," *IEEE*, vol. 86 pp. 184–187 (1986).

Buser, et al., "Silicon Pressure Sensor Based on a Resonating Element," *Sensors and Actuators A*, vol. 25–27, pp. 717–722 (1991).

Prak, et al., "Q–Factor and Frequency Shift of Resonating Silicon Diaphragms in Air,"*Sensors & Actuators A*, vol. 25–27, pp. 691–698 (1991).

Craine, et al., "A Digital Optically Multiplexed Charge Coupled Device (CCD) Based Deoxyribonucleic Acid (DNA) Sequence Reader," *Medical Imaging Ii*, vol. 914, pp. 512–517 (1988).

Misiura, et al., "Biotinyl and Phosphotyrosinyl Phosphoramidite Derivatives Useful in the Incorporation of Multiple Reporter Groups on Synthetic Oligonucleotides,"*Nucleic Acids Res.*, vol. 18, No. 15, pp. 4345–4354 (1990).

Kricka, "Chemiluminescent and Bioluminescent Techniques," *Clinical Chemistry*, vol. 37, No. 9, pp. 1472–1481 (1991).

Briggs, et al., "Sub–Femtomole Quantitation of Proteins with Threshold, for the Biopharmaceutical Industry," *BioTechniques*, vol. 9, No. 5, pp. 1–8 (1990).

Karger, et al., "Multiwavelength Fluorescence Detection for DNA Sequencing Using Capillary Electrophoresis," *Nucleic Acids Res.*, vol. 19, No. 18, pp. 4955–4962 (1991).

Karger, et al., "Imaging of Fluorescent and Chemiluminescent DNA Hybrids Using a 2–D CCD Camera," *New Technologies in Cytometry & Molecular Biology*, vol. 1206, pp. 78–89 (1990).

Briggs, "Biosensors Emerge from the Laboratory," *Nature*, vol. 329, p. 565 (Oct. 1987).

Knight, et al., "Nonradioactive Nucleic Acid Detection by Enhanced Chemiluminescence Using Probes Directly Labeled with Horseradish Peroxidase," *Analytical Biochemistry*, vol. 185, pp. 84–89 (1990).

Hollis, et al., "A Swept–Frequency Magnitude Method for the Dielectric Characterization of Chemical and Biological Systems," *IEEE Trans. on Microwave Theory and Techniques*, vol. MTT–28, No. 7, pp. 791–801 (Jul. 1990).

Neff, et al., "Two–Dimensional Spatial Light Modulators: A Tutorial," *Proceedings of the IEEE*, vol. 78, No. 5 (1990).

Hornbeck, "Deformable–Mirror Spatial Light Modulators," *SPIE Critical Reviews Series*, vol. 1150, p. 86 (1990).

Grant, et al., "Dielectric Behavior of Biological Molecules in Solution," *Clarendon, Pr., Oxford*, pp. 2, 4, 217–220.

Hullidy, et al., *Physics*, New York, John Wiley & Sons, 1978, p. 658.

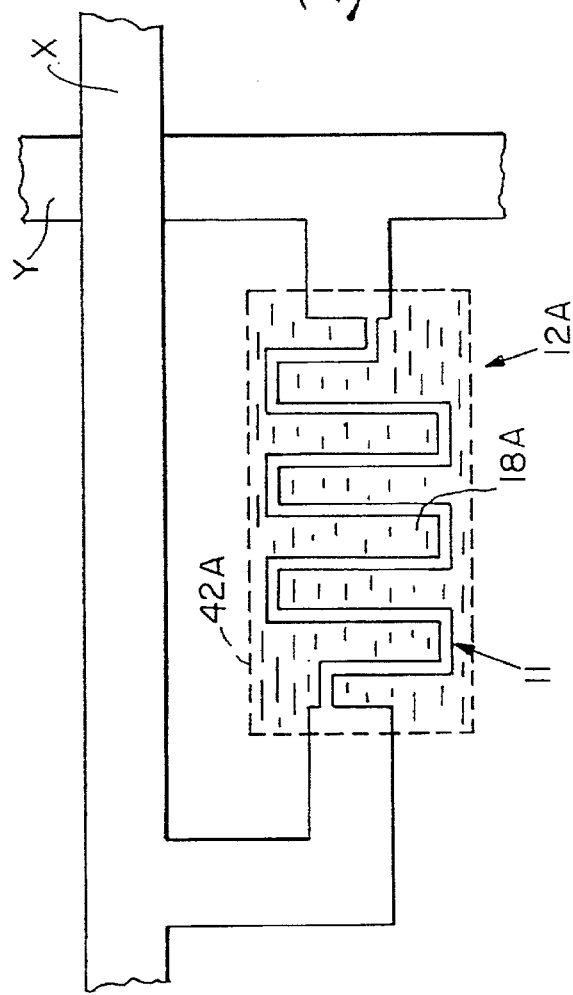
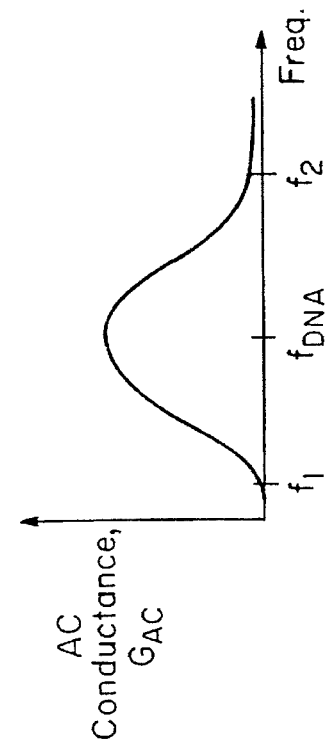
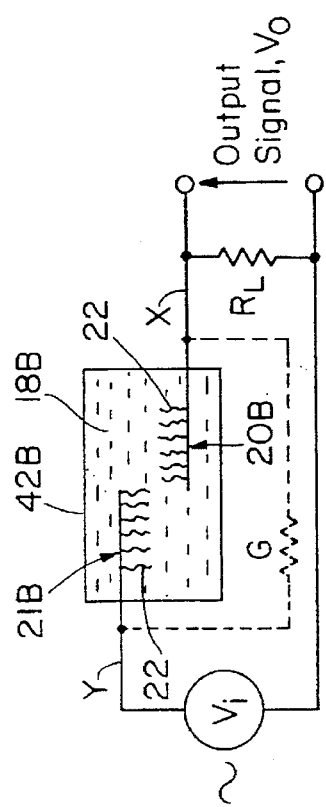

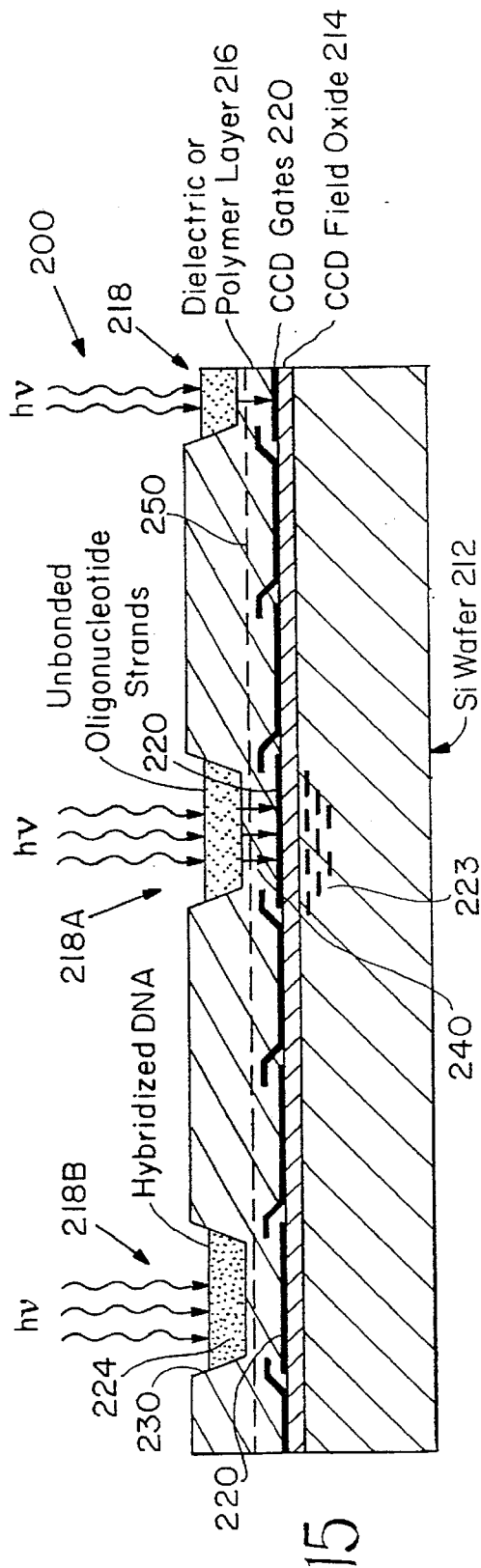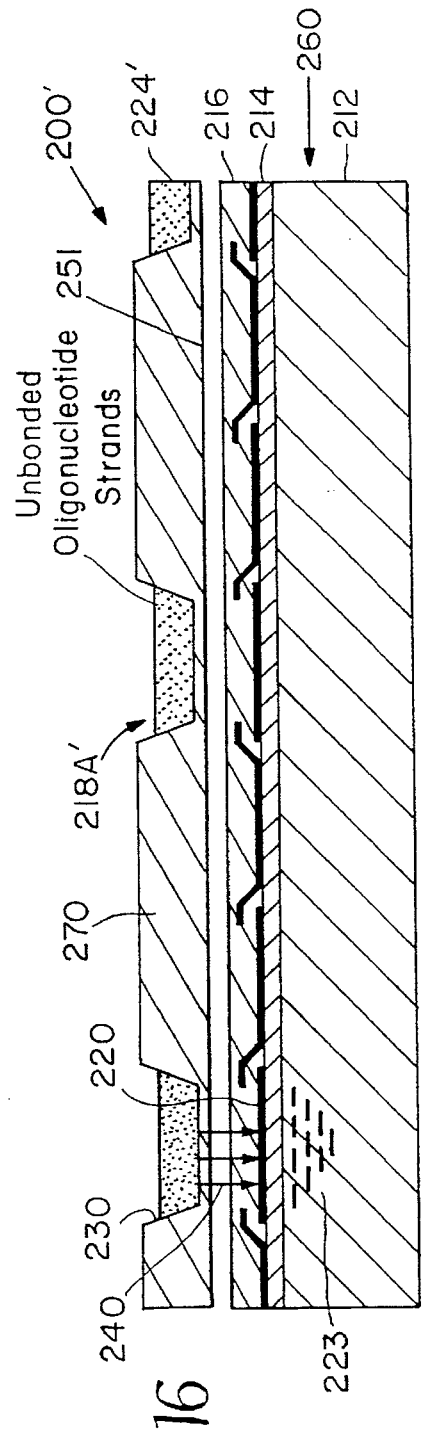
Fig. 15
Fig. 16

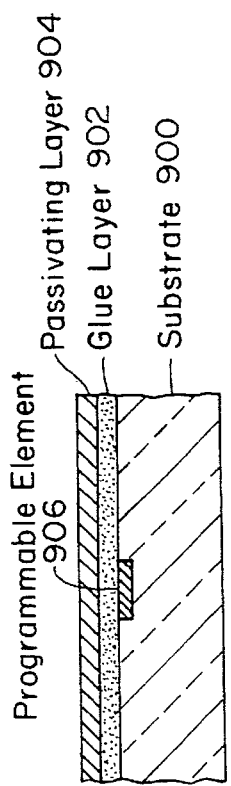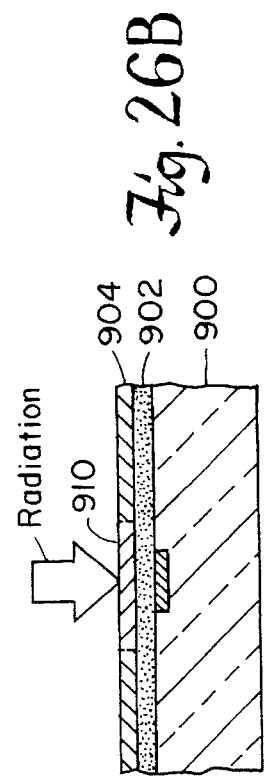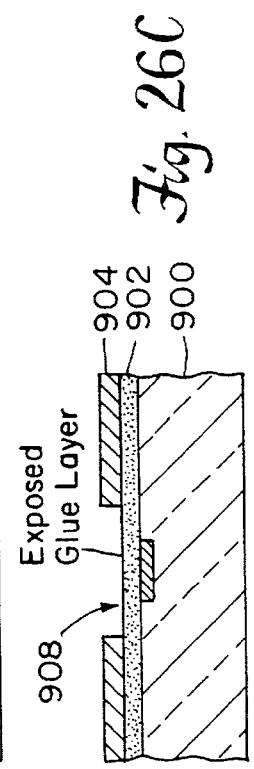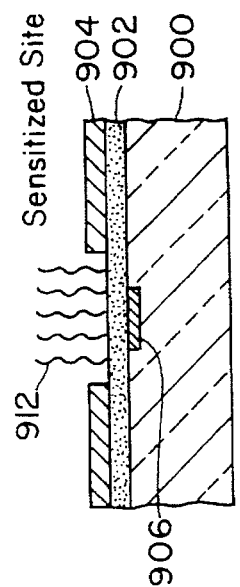
Fig. 26A  Fig. 26B  Fig. 26C  Fig. 26D
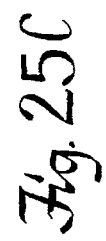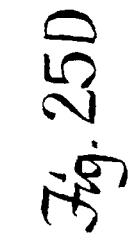
Fig. 25A  Fig. 25B  Fig. 25C  Fig. 25D

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ATCGCTTACG GTAATC                            1 6

OPTICAL AND ELECTRICAL METHODS AND APPARATUS FOR MOLECULE DETECTION

RELATED APPLICATIONS

This application is a divisional of co-pending application Ser. No. 07/872,582 filed Apr. 23, 1992, which is Continuation-in-Part of U.S. Ser. No. 07/794,036, filed Nov. 19, 1991 now abandoned and entitled METHOD AND APPARATUS FOR MOLECULE DETECTION.

GOVERNMENT SUPPORT

The Government has rights in this invention pursuant to Contract Number F19628-90-C-0002 awarded by the Department of the Air Force.

BACKGROUND OF THE INVENTION

In many applications, it is desirable to detect the presence of one or more molecular structures in a sample. The molecular structures typically comprise ligands, such as, cells, antibodies and antiantibodies. Ligands are molecules which are recognized by a particular receptor. Ligands may include, without limitation, agonists and antagonists for cell membrane receptors, toxins, venoms, oligo-saccharides, proteins, bacteria, and monoclonal antibodies. For example, a DNA or RNA sequence analysis is very useful in genetic and disease diagnosis, toxicology testing, genetic research, agriculture and pharmaceutical development. Likewise, cell and antibody detection is important in disease diagnosis.

A number of techniques have been developed for molecular structure detection. In DNA and RNA sequence detection, two procedures are generally used, autoradiography and optical detection. Autoradiography is performed using $^{32}P$ or $^{35}S$. For DNA sequence analysis applications, nucleic acid fragments are end labeled with $^{32}P$. These end labeled fragments are separated by size, then exposed to x-ray film for a specified amount of time. The amount of film exposure is directly related to the amount of radioactivity adjacent to a region of film.

The use of any radioactive label is associated with several disadvantages. First, prolonged exposure to radioactive elements increases the risk of acquiring genetic diseases, such as cancer. As such, precautions must be implemented when using radioactive markers or labels to reduce the exposure to radioactivity. Typically, workers must wear a device to continually monitor radioactive exposure. In addition, pregnant females should take additional precautions to prevent the occurrence of genetic mutations in the unborn.

The conventional radioactive detection scheme has sensitivity limitations in both the temporal and spatial domains. The use of radioactive labelling currently has a spatial resolution of one millimeter. Additional hardware and software are required to reduce the spatial resolution below one millimeter.

The sensitivity of detection utilizing autoradiographic film is directly related to the amount of time during which the radioactive labelled fragments are exposed to the film. Thus, the exposure time of the film may range from hours to days, depending upon the level of radioactivity within each detection test site. A β scanner may drastically reduce the time required for film exposure during radiography. However, the use of the β scanner significantly increases the expense associated with this type of detection, and has intrinsically poor spatial resolution.

Optical detection of fluorescent labelled receptors has also been utilized to detect molecular binding. Briefly, for DNA sequence analysis applications, a base-specific fluorescent dye is attached covalently to the oligonucleotide primers or to the chain terminating dideoxynucleotides used in conjunction with DNA polymerase. The appropriate absorption wavelength for each dye is chosen and used to excite the dye. If the absorption spectra of the dyes are close to each other, a specific wavelength can be chosen to excite the entire set of dyes.

A particular optical detection technique involves the use of a dye, for example, ethidium bromide, which stains duplexed nucleic acids. The fluorescence of these dyes exhibits an approximate 20-fold increase when it is bound to duplexed DNA or RNA, when compared to the fluorescence exhibited by unbound dye, or dye bound to single-stranded DNA. This type of dye is used to detect the presence of hybridized DNA (or RNA) during a hybridization experiment. Although the use of conventional optical detection methods increases the throughput of the sequencing experiments, the disadvantages are serious.

Therefore, a need has arisen in the industry for a safe, low-cost, fast and accurate method and apparatus for detecting molecular structures at reduced complexity.

SUMMARY OF THE INVENTION

In accordance with the present invention, a method and apparatus for detecting the presence of molecular structures in predetermined test sites is provided which substantially eliminates or prevents the disadvantages and problems associated with prior devices.

In an electrical embodiment of the present invention, a substance having a molecular structure is applied to a plurality of test sites, each test site having a probe formed therein capable of binding to a known molecular structure. Electrical signals are applied to the test sites, and electrical properties of the test sites are detected to determine whether the probe has bonded (hybridized) to, or with, an associated molecular structure.

The test sites are monolithic structures formed on, or in, semiconductor chips or wafers using very large scale integrated (VSLI) circuit methods. This results in a low-cost, small-size, testing device which may be inexpensive enough to be disposable after use.

Hybridized molecules can be detected, in accordance with one embodiment of the invention, by sensing the change in dissipation of a capacitor formed at the test site, or by sensing the change in AC conductance of a test site when hybridized molecules are present. Alternatively, by forming a transmission line between two electrodes at each test site, the presence of hybridized molecules can be detected by measuring the RF loss associated with the formation of hybridized molecules at the test site.

In another embodiment, micro-machined resonators are formed in each test site and the change in resonant frequency, or the change in the Quality Factor (Q) of the resonator, caused by formation of hybridized molecules may be measured to determine which sites contain hybridized molecules.

In an alternate optical embodiment of the invention, a charge-coupled-device (CCD) array is provided, with each electrode of the CCD array aligned with a respective adjacent test site. Light attenuation, caused by greater absorption of illuminating light in test sites with hybridized molecules is used to determine the sites with the hybridized molecules. The CCD array can be integrated with a corresponding test site array. Alternatively the test site array may be a separate disposable plate.

The probes within each test site are all identical, but differ from test site to test site. The probes for DNA or RNA sequence testing are generally formed of oligonucleotide strands. In accordance with another embodiment of the invention, an optical direct patterning system is used to perform localized sensitization of the microarray or localized synthesis of oligonucleotide strands at each test site to customize or differentiate each of the probe strands.

A further understanding of the nature and advantages of the invention herein may be realized with respect to the detailed description which follows and the drawings described below.

BRIEF DESCRIPTION OF THE DRAWINGS

FIG. 8 is a plan view of an alternate test site embodiment using a meander transmission line.

FIG. 9 is a schematic of a test site detection system using an applied AC input voltage $V_i$ having a frequency range $f_1$ to $f_2$.

FIG. 10 is a plot of the AC conductance of the test site to the input voltage $V_i$.

FIG. 15 is a schematic cross-section of an alternate embodiment in which the test sites are formed with an underlying CCD array.

FIG. 16 is a view as in FIG. 15 wherein the test sites are formed in a disposable plate and associated with a separable CCD array.

FIGS. 25A–D is a series of cross-sectional drawings illustrating an alternate method of array sensitization.

FIGS. 26A–D is a series as in FIGS. 25A–D depicting an alternative array sensitization method.

DETAILED DESCRIPTION OF THE INVENTION

I. General Overview of System

A preferred embodiment of the present invention and its advantages may be understood by referring to FIGS. 1–4 and 4A–4C of the drawings, in which like numerals are used for like and corresponding parts of the various drawings.

Figure 2:
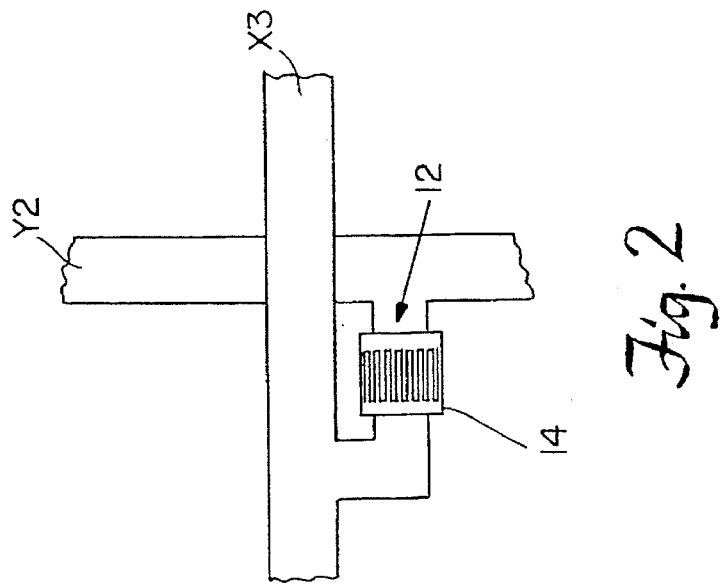
FIG. 2 is an enlarged view of a portion of FIG. 1.
Figure 1:
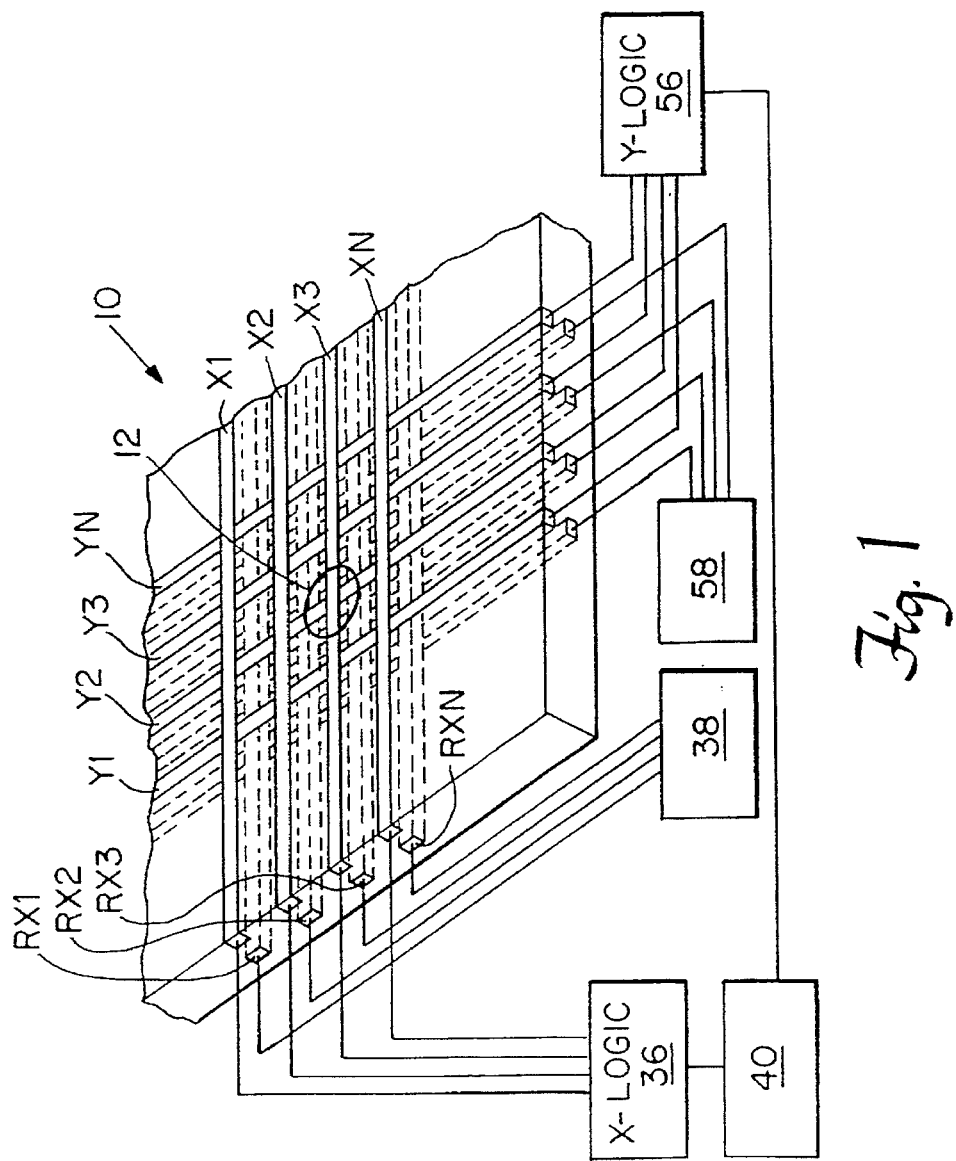
FIG. 1 is a schematic partial perspective of a microelectronic sensor array in accordance with a preferred embodiment of the invention.

FIG. 1 illustrates a preferred embodiment of the present invention used in connection with RNA and DNA sequencing. As described hereinbelow, the present invention may also be used for cell detection and antibody detection or detection of any hybridized molecule.

The sequencer 10 comprises an X-Y array of test sites 12 electronically addressable by conductive leads X1, X2, X3 - - - XN on the X-axis and conductive leads Y1, Y2, Y3 - - - YN on the Y-axis. X-logic circuitry 36 for sequentially addressing each X-line is coupled to detection and recognition circuitry 40. Similar circuits 56 are coupled to the Y-lines Y1 - - - YN. The array 10 and X and Y logic circuitry 36 and 56 and circuitry 40 may all be implemented on a single semiconductor chip depending upon cost trade-offs.

The test sites 12, described in greater detail hereinbelow, are formed in a semiconductor wafer using semiconductor photolithographic processing techniques. Each test site contains a plurality of probes 22 (See FIG. 4) which are capable of binding to known molecular structures (hereinafter "target(s)"). The targets could comprise, for example, biopolymers such as polynucleotides, DNA, RNA, cells, antibodies or antiantibodies. For the case of a RNA or DNA sequencer, the synthetic probes may comprise, for example, oligonucleotides. All the probes 22 in a given test site are identical. But, the probes in respective test sites 12 differ in a known sequence for simultaneous detection of a plurality of different targets (or subsequences within a target molecule) within a single array 10.

When a sample substance containing the targets in an electrolyte solution 18 is poured onto the array 10, the targets bind with associated probes 22 within a plurality of wells 42 formed in each test site 12. After sufficient time for binding, the surface of the array 10 is rinsed to remove excess targets or other unbound molecular structures. The remaining target structures will be, for the most part, bound to the probes attached to the microfabricated array 10 at specific test sites 12. Each test site 12 is then interrogated electronically by the logic circuitry 36 and 56 to determine whether targets have bound in that test site. Test sites having bound targets, i.e., hybridized molecules, will have changed electrical parameters, which may be detected by detection circuitry 40 coupled to the test sites over the X and Y leads. Thus, by electronic addressing, the detection of specific target/probe bindings is achieved at each test site 12 within the microfabricated array 10, thereby determining the composition of the targets that remain present after washing.

For the example of DNA sequencing, recognition circuit 40 performs a sequence analysis described in connection with FIG. 21 based upon the composition of the targets (nucleic acids) detected by the circuitry 40.

Note: Circuit 40 is preferably coupled to the test sites by transistor switches (not shown) using row and column addressing techniques employed, for example, in addressing dynamic random access memory (DRAM) or active matrix liquid crystal display (AMLCD) devices.

II. Test Sites

The test sites 12 are preferably formed as monolithic structures on a wafer or substrate 34 preferably of single crystal Si or equivalent, such as glass, quartz, alumina etc. First, an optional resistor array of X and Y resistors 32 coupled to leads RX1, RX2, RX3 - - - RXN and RY1, RY2, RY3 - - - RYN (as shown in FIG. 1) may be formed by metal evaporation or sputtering of appropriate material on substrate 34. The leads are coupled at one end to resistors 32 formed of resistive material, such as nichrome, tungsten or platinum, located beneath each test site and at another end to X-resistor-logic circuit 38 and Y-resistor-logic circuit 58 for probe synthesis purposes to be described later.

Alternatively, resistors 32 may be formed of deposited doped polysilicon, tungsten or tantalum or platinum silicides, nitrides or oxynitrides, by well-known techniques, such as chemical vapor deposition (CVD), molecular beam epitaxy (MBE), metal organic CVD (MOCVD) or similar semiconductor process.

Figure 5A:
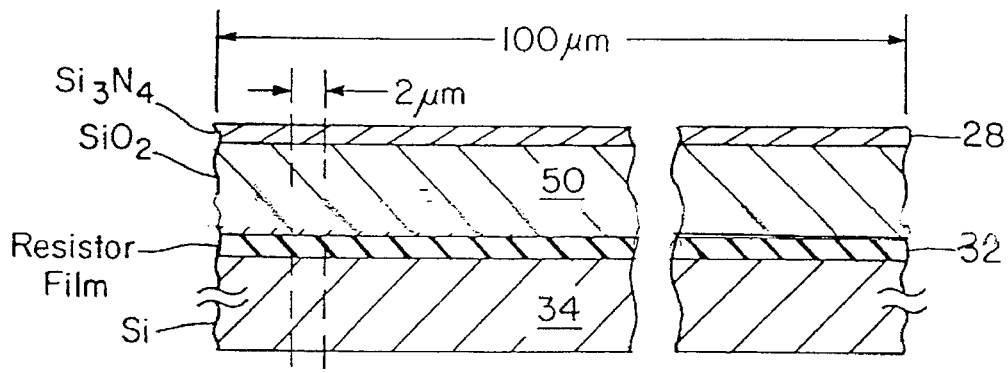
FIGS. 5A–5D are schematic cross-sectional process diagrams showing important steps in forming test sites.

Referring to FIGS. 5A–5D, after the resistors 32 and resistors RX and RY address lines are formed, a thick (approximately 5000 Å) $SiO_2$ film 50 is then formed by CVD on layer 32. A thin layer 28 of about 500 Å of a mask material, such as $Si_3N_4$, is then formed on $SiO_2$ film 50, for example by Chemical Vapor Deposition (CVD) (FIG. 5A).

NOTE: In FIGS. 5A–5D, only a section of wafer 34 occupied by a single test site 12 is shown. It should be understood that many more, i.e., about 7+ million such sites can be fabricated and tested on a single three inch Si wafer using present state of the art technology.

Figure 3:
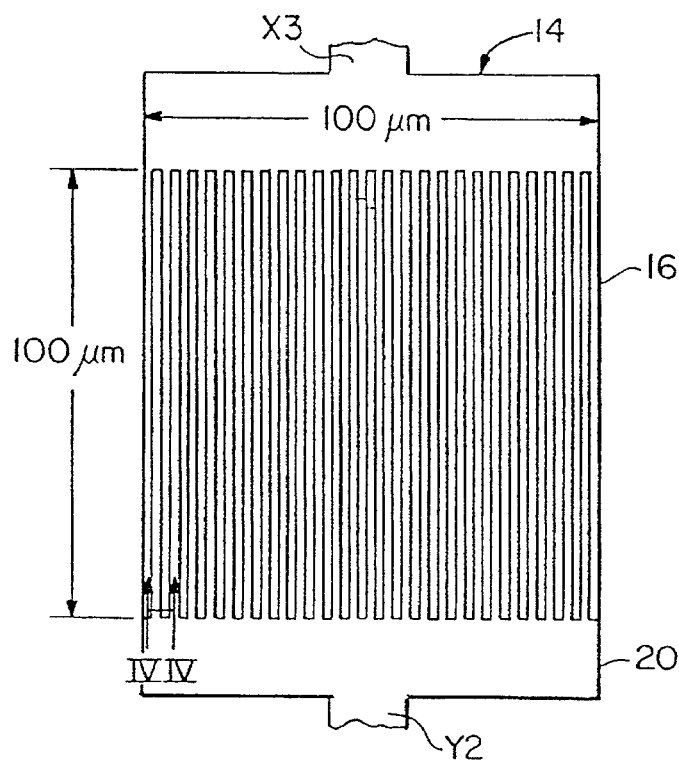
FIG. 3 is an enlarged view of the electrode portion of FIG. 2.
Figure 4:
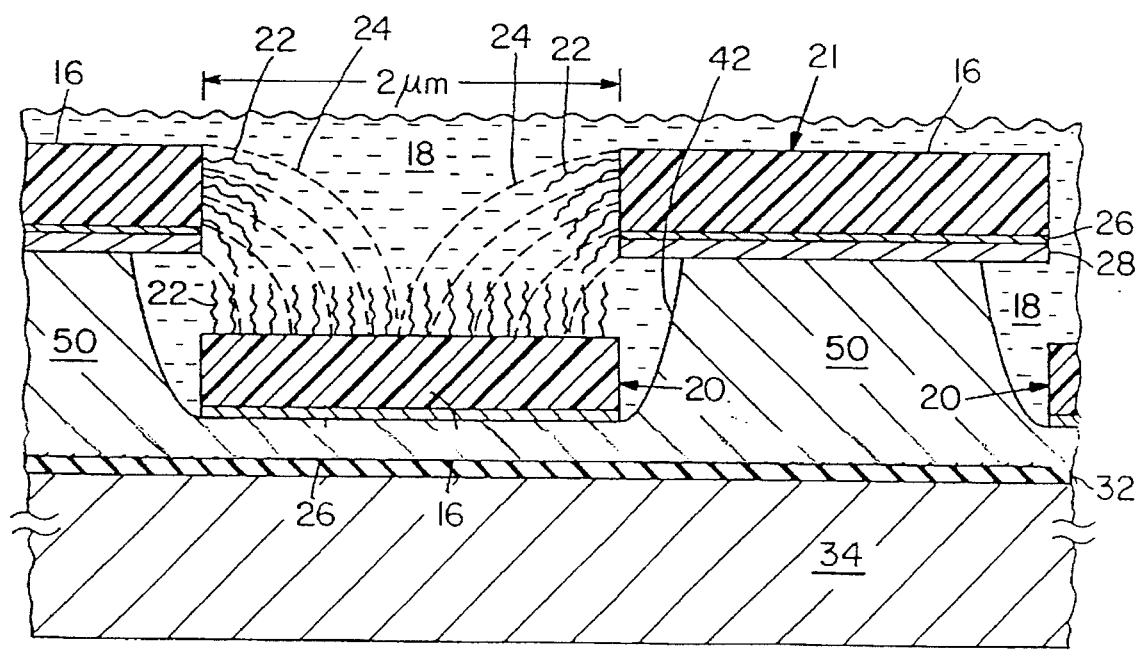
FIG. 4 is a section taken along lines IV—IV of FIG. 3.

The precursor structure shown in the sectional view of FIG. 5A is next processed to form an upper and lower digitated electrode structure, a portion of which is shown in the cross-section IV—IV of FIG. 3, shown in detail in FIG. 4.

Figure 5B:
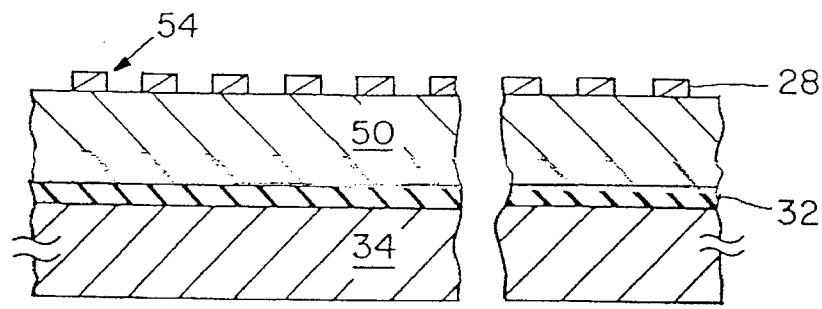
Figure 5C:
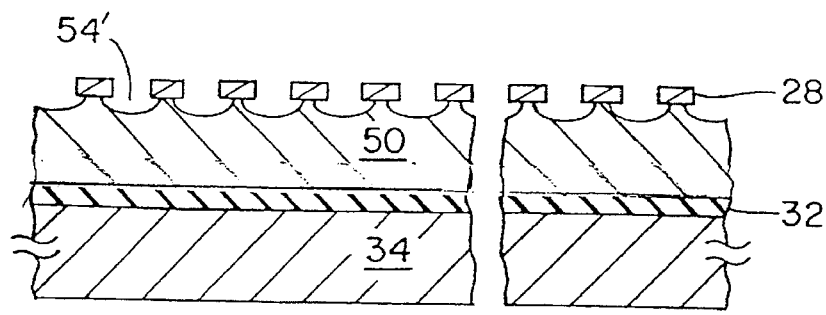
Figure 5D:
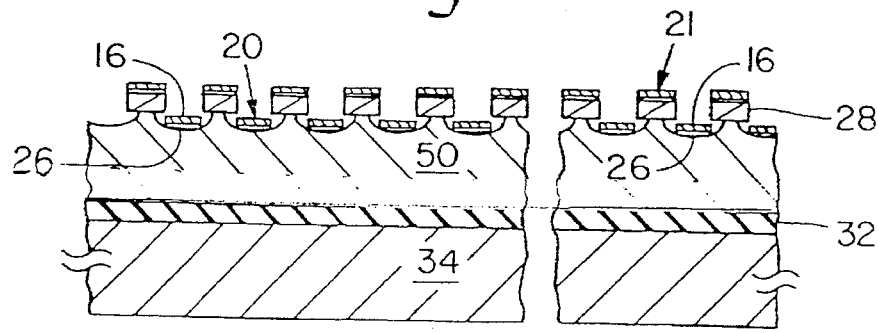

First, openings 54, about 2 microns wide, are formed in $Si_3N_4$ layer 28 by photolithography and reactive ion etching (FIG. 5B). Next, about 4000 Å of $SiO_2$ layer 50 is wet etched with an acid solution, such as buffered HF, to form recesses 54' (FIG. 5C).

The upper and lower electrodes 21 and 20, respectively, are then formed by successive electron beam evaporation of an adhesion layer (300 Å) of Ti 26 followed by 2000 Å of contact metallization (Au) 16. Note that the lateral edges of the remaining $Si_3N_4$ film 28 serve as a precise self-aligning mask for defining the width of the fingers of lower electrode 20, thereby enabling close spacing between the upper and lower electrodes without shorting. Hence, the well sites can be tested at low applied voltages. The electrodes also occupy a relatively large volume of the well, vis-a-vis the volume of the aqueous DNA solution with target DNA 18 (See FIG. 4). Most importantly, the spacing between the upper and lower electrodes is of the order of the length (or diameter in solution) of the target DNA molecule. Therefore, the ratio of the target DNA to solvent in the interelectrode space is high, thereby giving greatest sensitivity to the presence or absence of the target DNA during an electrical measurement.

The length of the electrode fingers, as shown in FIG. 3 And FIG. 5A, is about 100 microns and the width of the set of electrodes is also about 100 microns, with each finger having a width of 2 microns, as shown in FIG. 4 and a spacing of 2 microns.

The interdigitated design packs a lot of electrode periphery and sample volume in a small area on the wafer. Its ratio of "sample" capacitance to parasitic capacitance caused by leads coming to the site is high.

Figure 6A:
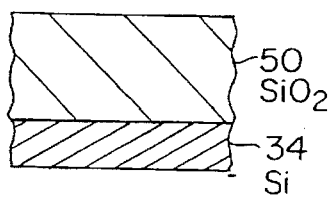
FIGS. 6A–6H are schematic cross-sectional process diagrams showing important steps in forming alternate embodiments of the test sites.
Figure 6B:
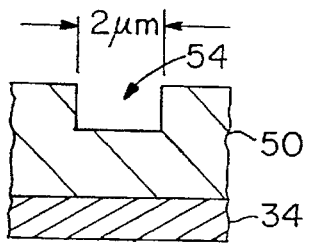
Figure 6C:
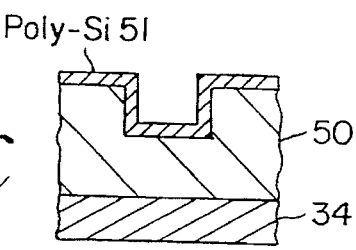
Figure 6D:
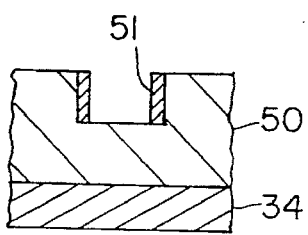
Figure 6E:
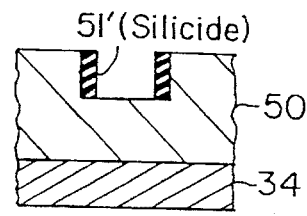

Referring now to the schematic sectioned sequence views of FIGS. 6A–6F, an alternate process for fabricating test sites 12A will be described in connection therewith. Note: Unless specified, the layer thicknesses are as indicated in FIGS. 5A–5D. An $SiO_2$ layer 50 is grown on a Si substrate 34 (FIG. 6A). The $SiO_2$ film is etched to form an array of 2 micron wide wells 54 periodically spaced from one another by 2 microns (FIG. 6B). Photolithography and reactive ion etching to a depth of about 0.5 microns is used to form the wells 54. A poly-Si film 51 of about 2000 Å is formed, for example, by CVD on $SiO_2$ layer 50 (FIG. 6C). The regions of film 51 at the bottom of the well and on the top surfaces is etched away by reactive ion etching (FIG. 6D) leaving sidewalls of polysilicon 51. The sidewalls are selectively metallized 51' by silicidation using W, Ti or Pt (FIG. 6E). Finally, Ni or Au electrodes 61 are formed on the silicide sidewalls 51' by electroless plating (FIG. 6F).

Figure 6F:
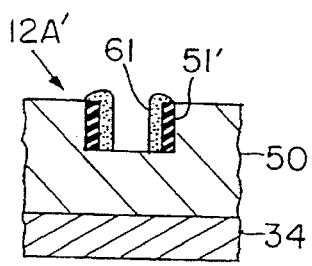
Figure 6G:
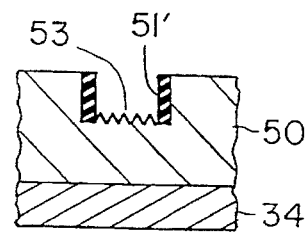
Figure 6H:
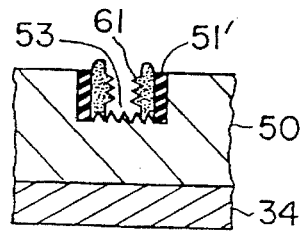

FIGS. 6G and 6H are alternate embodiments of FIGS. 6E and 6F respectively. In FIG. 6G the bottom of the test site is textured, in this case by corrugations, to increase the surface area; whereas in FIG. 6H both the electrode 61 and the bottom wall is corrugated. This texturing increases the surface area of a given site, allowing more probes to be attached for greater sensitivity.

III. Electronic Hybridization Detection Methods

A. General Methodology

The sensor array 10 described in FIGS. 1–4 may, in accordance with the invention, be used as a genosensor to sense the presence or absence of target DNA strands in each test site 12.

In a decoding test, a large number of relatively short oligonucleotide strands (probes 22) are grown or placed in each test site 12, such that one end of the strand is attached to one or more surfaces of the site. The coding sequence of all the strands in a given site 12 is known and is identical, and the coding sequence of each site is different and unique in the array. A solution 18 containing long strands of unknown (target) DNA is then washed across the chip. Ideally, the unknown DNA bonds tightly to the oligonucleotide strands 22 in any site that contains the complement to a portion of its own code sequence, but in no other well. Practically, some weakly bound target mismatches occur, but these can be alleviated by rinsing the well with an appropriate solution at an appropriate ion concentration and temperature. Consequently, after a rinse, a number of the wells in the array will contain a significant amount of this bonded or hybridized DNA, and the rest will contain only the original oligonucleotide strands in an aqueous solution. The wells are then interrogated electrically in sequence using the electrodes 16 and 20 in each site. The sites that contain hybridized DNA are recorded. For example, sites without hybridized DNA will have different electrical properties than those with hybridized DNA and will not be recorded. At the resonant frequency of a DNA molecule in aqueous solution, the imaginary part $\epsilon''$ of the complex relative permittivity $\epsilon_r = \epsilon' - j\epsilon''$ of the solution can be approximately a factor of 10 to 100 times larger than its value for an aqueous solution without the DNA. Methods B, C, D, and E below are designed to measure or detect this difference in $\epsilon''$ at each site 12. From this data base, a computer "overlapping" or "neural network" algorithm in circuit 40 reconstructs the entire coding sequence of the unknown DNA.

B. Dissipation Factor Test

Figure 7:
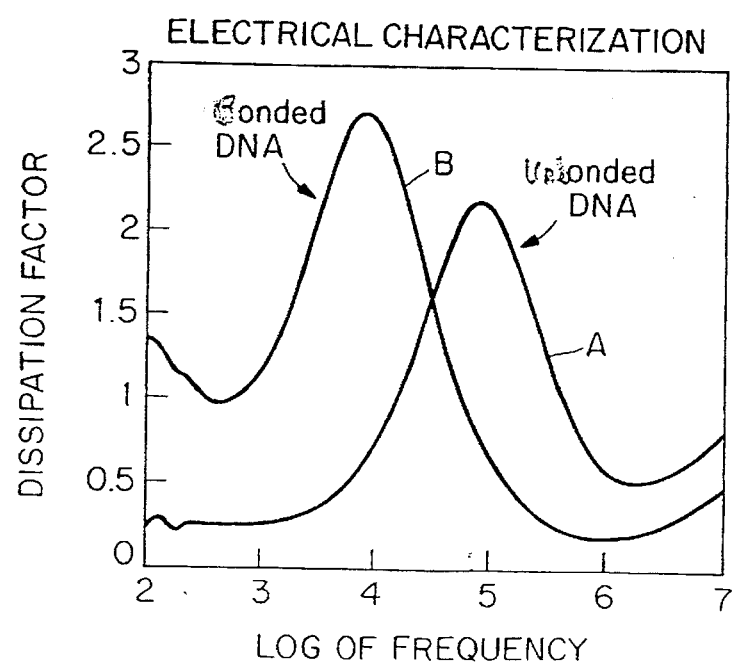
FIG. 7 is a plot of dissipation factor versus frequency for bonded test sites (Curve A) and unbonded test sites (Curve B).

FIG. 7 is a plot of dissipation factor versus the log of frequency for bonded (hybridized) DNA (curve B) and unbonded DNA (curve A) showing how the dispersion factor $D=\epsilon''/\epsilon'$ differs, depending upon whether the DNA is bonded or not. Note: Depending upon the particular samples measured, the curves of FIG. 7 may be reversed, i.e. curve B could represent unbonded DNA. This difference in dispersion factor is used to determine the presence or absence of hybridized DNA at a test site formed as in FIGS. 1–6. The dissipation factor at each test site is measured by well-known instrumentation such as an LCR meter in circuit 40. The meter is successively coupled to each site 12 via logic circuits 36 and 56.

C. AC Conductance Test

Similarly, the presence or absence of hybridized DNA can be detected by measuring the AC conductance $G_{AC}=\epsilon''A/d$ at each test site; wherein A is the effective area of one electrode and d is the effective distance between electrodes. At the relaxation frequency of a given DNA molecule, the AC conductance should be as much as 100 times or more larger than the conductance when no DNA is present. FIG. 9 is a schematic representation of how this test may be conducted. A pulsed or frequency-scanned waveform is applied across electrodes 21B and 20B of each test site 12B. Probes 22 are formed on each electrode and an aqueous solution of target molecules is formed in the wells 42B of the test sites 12B. The presence of hybridized DNA is detected at a resonant frequency of DNA as shown in FIG. 10. An LCR meter may be used to measure G or R=1/G at a discrete frequency. Alternatively, as discussed in connection with FIGS. 9 and 10, G can be measured as a function of frequency.

D. Transmission-Loss Detection Test

Signal loss on a transmission line is also sensitive to $\epsilon''$. By incorporating a transmission line 11 between the X and Y lines at each test site (as shown in FIG. 8) electrical detection of hybridized molecules, such as DNA, can be accomplished by scalar measurement of the RF loss of an electromagnetic wave passing along the line 11 at each test site 12A. Line 11 may comprise a micro-miniature version of stripline, microstrip, waveguide, coplanar waveguide, slotline, or coaxial line. To achieve maximum sensitivity with this method, the test site well 42A is made relatively wider and/or longer than the wells in FIG. 4, and the length of the transmission line in the well is maximized by forming it in a meandering pattern.

E. Pulse and Chirp Method of Detection

Figure 11:
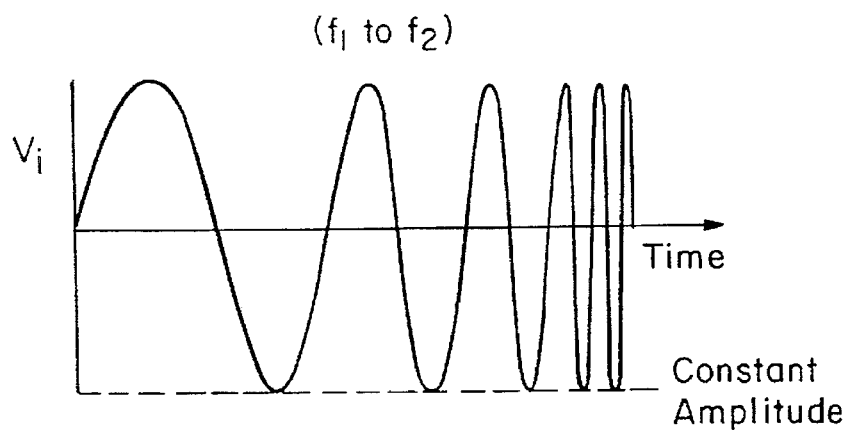
FIG. 11 is a plot of $V_i$ versus time for a constant amplitude signal which is swept from a lower frequency $f_1$ to a higher frequency $f_2$.
Figure 12:
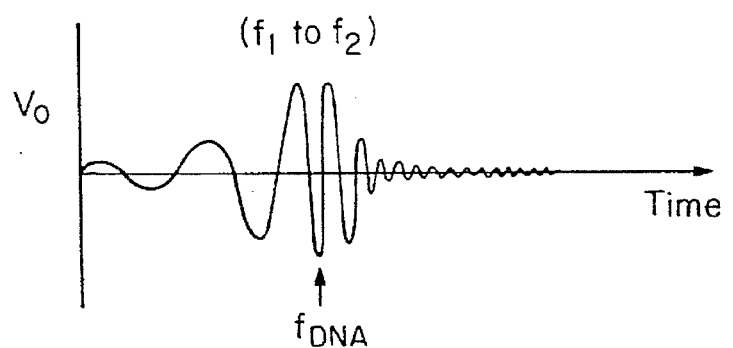
FIG. 12 is a plot of the sensed output voltage $V_o$ from the test site in response to the input voltage waveform of FIG. 11.
Figure 13:
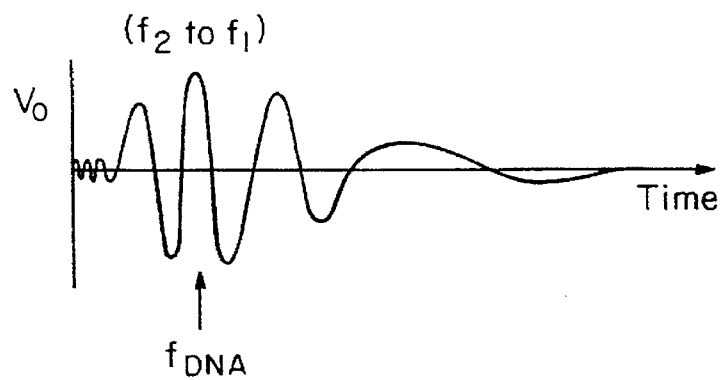
FIG. 13 is a plot of the sensed output voltage $V_o$ from the test site in response to an input waveform $V_i$ which descends from $f_2$ to $f_1$.

As shown in FIG. 11, a frequency scanned or chirped voltage waveform $V_i$ may be applied across the electrodes at each site and the resultant response waveform $V_o$ (FIG. 12 or FIG. 13, depending upon whether frequency is increasing or decreasing) is analyzed to determine the presence of hybridized DNA as indicated by a maxima at a hybridized DNA frequency. The measurement of the relaxation frequency of the hybridized DNA using a frequency-scanned waveform gives additional information about the properties of the hybridized DNA, e.g., crosslinked versus non-crosslinked.

F. Micromechanical Resonator Detection Methods

Figure 14:
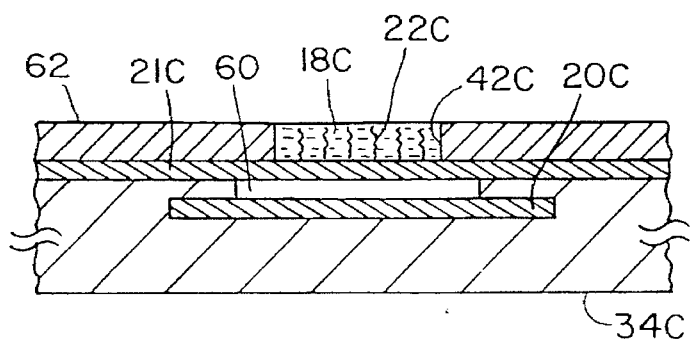
FIG. 14 is a schematic sectional view of a test site fabricated with a mechanical resonator structure.

In this embodiment, a plurality of mechanical resonator structures are formed in test sites formed in silicon wafer 34C, as shown in FIG. 14. The resonator structure comprises a lower metal sensor electrode 20C extending in the X-direction and an upper membrane resonator film 21 preferably of silicon nitride or metal such as tantalum extending along a Y-direction in the plane of the wafer. Typically the membrane size is about 100 microns in diameter or width/length. A dielectric gap 60, preferably of air, is formed between the upper and lower members 21C and 20C.

A test site well 42C is formed over membrane 16C and probes 22C formed in the well surfaces. Target DNA solution 18C is dispensed into the test well 42C. The mechanical cavity 60 between the upper and lower electrodes 16C and 20C forms a resonator. This resonator has a resonant frequency in the kilohertz to multimegahertz range with a narrow resonant linewidth.

An RF signal propagated across each resonator will produce a characteristic high Q response with a narrow linewidth. A shift in either Q or resonant frequency indicates the presence of hybridized molecules on the resonator surface electrode membrane 21C.

Membrane electrode 21C may be formed of a thin film of silicon nitride using chemical vapor deposition at a well controlled silicon to nitrogen ratio and controlled elevated temperature to adjust the film tension when it is cooled to room temperature. Membranes can be formed on unpatterned silicon wafers then released as free standing structures by etching out a silicon window from the back side. Examples of mechanical resonators and details of this construction for use, as above, are given in Buser et al. "Silicon Pressure Sensor Based On a Resonating Element" Sensors and Actuators, A, 25–27 (1991) 717–722 and Prab et al. "Q-Factor and Frequency Shift of Resonating Silicon Diaphragms in Air" Sensors and Actuators A, 25–27 (1991) 691–698.

H. Surface Acoustic or Electromagnetic Wave Detector Methods

Figure 23:
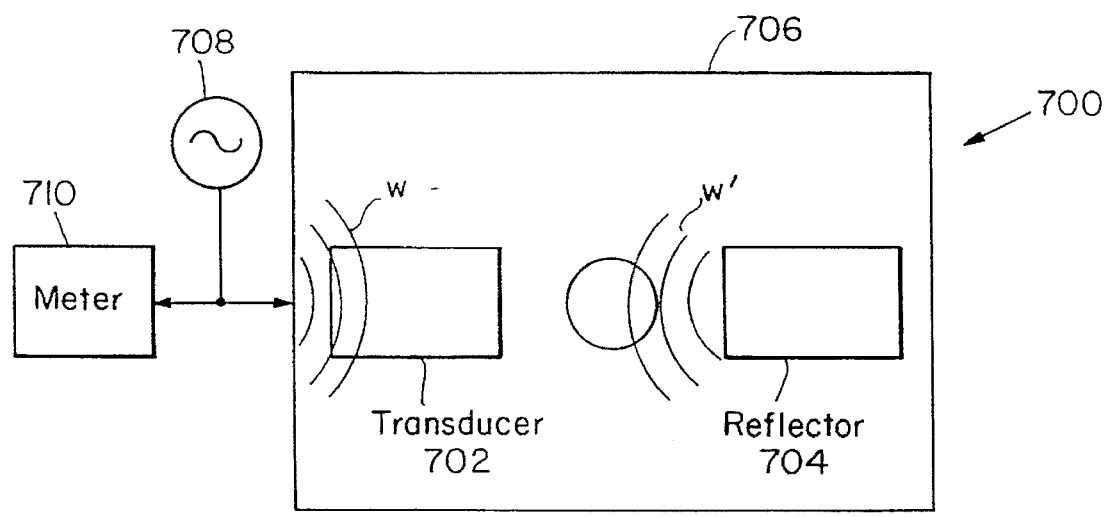
FIG. 23 is a schematic representation of a surface-acoustic-wave embodiment of the invention.

A similar class of resonant array detectors can be formed of surface wave devices, for example, by employing surface acoustic waves (SAW) or surface electromagnetic waves. In the case of a SAW detector, as shown in FIG. 23, a resonant structure 700 is formed using an acoustic transducer 702 and a SAW reflector 704. A scanned frequency wave W from source 708 is launched across the acoustic medium 706 (preferably a lithium niobate or quartz crystal). The reflector 704 induces discrete cavity resonances which are detected by measuring, in meter 710, the power dissipated by the transducer. Test sites 712 are formed on the medium. Each site may have an associated transducer and reflector or a multiplexer may be formed on the substrate to couple a single transducer to multiple sites. Sites with bonded target/probe pairs shift the resonant frequencies. Hence, sites with bonded probes become detectable. The transducer 702 may be applied as an interdigitated aluminum thin-film structure evaporated on the lithium niobate crystal substrate 706. The reflector 704 can be an aluminum thin-film grating. Standard photolithography and evaporation are used to pattern these structures.

Alternatively, the phase of the SAW wave, after passage through a test site, may be compared in a transmission line to a reference transmission line formed in the substrate and the phase shift caused by bonding used to determine which sites have bonded molecules.

IV. OPTICAL HYBRIDIZATION DETECTION METHODS

A. Monolithically Integrated CCD Imager/Readout

Referring now to the cross-sectional schematic view of FIG. 15, an alternate embodiment of the invention will now be described which uses optical detection by means of a monolithically integrated charge-coupled device (CCD) sensor to detect the presence or absence of hybridized molecules in a test well.

Arrays 200 of charge-coupled devices (CCD's) are formed as integrated circuits on silicon wafers 212 to perform an imaging function. The CCD array 200 reads-out charge formed beneath detector gate electrodes 220 when light photons (hʋ) impinge on non-hybridized test sites 218A.

The wavelength of the light (hʋ) is selected to match a known absorption line of one of the hybridized DNA. The sensitivity of the method is increased through the use of absorbing dyes such as ethidium bromide which selectively intercalate into hybridized DNA. The light passes relatively unattenuated through the non-hybridized test site 218A, but is attenuated by the bound molecules or the dye in the hybridized test sites 218B.

The light photons induce a charge 223 in the silicon wafer 212 beneath the electrode 220 underlying the non-hybridized wells 218A. Such charges are then read out of the CCD array in the well-known manner and processed to identify the test sites containing hybridized molecules.

The CCD array genosensor 200 of FIG. 15 is formed by growing a field oxide layer 214 of $SiO_2$ on a Si epitaxial wafer/substrate 212. CCD gate electrodes 220 are then formed by sputtering of metals such as tantalum or tungsten on the oxide 214. A dielectric or polymer layer 216, preferably of light transmissive material such as silicon nitride or glass, $SiO_2$ or polyimide is then formed over the electrodes. Wells 230 are then formed in the layer 216 directly above the gate electrodes 220. The wells are passivated with a thin protective layer (not shown), such as silicon nitride or aluminum oxide to prevent degradation of the CCD device due to exposure to aqueous solution. Standard lithographic techniques are used to align the gates and wells.

Probes (not shown) are then formed in the wells 230 to individualize each test site 218 prior to introduction of the aqueous test solution 224.

In an alternative embodiment, the target molecules are tagged with labels using any of the well-known labelling mechanisms, such as fluorescent dyes, radioisotopes or chemiluminescence. The CCD array is formed as shown in FIG. 15, with an epitaxial Si substrate 212, a field oxide 214, CCD gates 220, dielectric layer 216 and wells 230.

The test regions are each provided with unique probes (not shown) and test solutions 224 containing tagged targets. The targets may be tagged with luminescent or chemiluminescent or radiological material. The test sites containing hybridized tagged DNA emit radiation which is detected by the occurrence of an accumulation of charge in a region beneath a respective CCD gate 220.

Preferably, in the labelled target embodiment a filter 250, which may be formed of an aluminum or tungsten metal grating or dielectric multilayer interference filter, is formed in the dielectric layer 216 between the well 230 and the metal electrode 220. The filter 250 is adapted to block the excitation radiation (hʋ) or $\alpha$, $\beta$, $\gamma$ particles and pass the secondary emission 240. The secondary emission is either light or other particles such as electrons stimulated by the excitation. The chemiluminescent approach involves the conversion of chemical energy into electromagnetic radiation. Preferred materials are stabilized 1,2-dioxetanes. Unlike other chemiluminescent modalities, enzyme catalyzed 1,2-dioxetane derivatives can produce a light signal that can last from hours to days. The wavelength of emitted light is near 477 nm, and the emission can be controlled by controlling the pH. At 477 nm, the quantum efficiency of the CCD to be employed is only approximately 13%; thus, the chemiluminescent signal may have to be enhanced. Methods of enhancement include the addition of water soluble macromolecules (e.g., bovine serum albumin) to enhance the chemiluminescent signal.

The advantages for using 1,2-dioxetanes are numerous. In addition to no radioactivity exposure, this method is relatively simple to perform (reagents and equipment are inexpensive). Finally, this method has a low background noise level and wide dynamic range.

In an alternative two-piece implementation as shown in FIG. 16 the probe site array 200' is formed on a separate thin transparent substrate such as a 10-mil-thick pyrex plate 270. This separate plate is marked with precision alignment features such as etched or printed gratings (not shown) to permit a precise automated overlay of the separated probe plate onto a separated CCD array 260. Each array location in the probe plate is sensitized with unique probes. The CCD array is then fabricated with or without the blocking filter 250 of FIG. 15. In one embodiment, an analysis is made by bringing the probe plate into registered close proximity over the CCD array without using a lens to image the plate onto the CCD. Irradiation of the plate is as in either of the embodiments discussed above in connection with FIG. 15. A further alternative is to image the separated probe plate 200' onto the CCD array 260 using a lens. This would allow a greater separation between the plate and the CCD array, for the case in which secondary fluorescence is used, and also allows separation of the excitation and fluorescence by obliquely exciting the probe plate. Imaging with magnification or demagnification is possible so that the probe plate dimensions can be optimized separately from the CCD.

The CCD device used to monitor the probe array for any of these geometries can be of the conventional variety and sensitive to the ultraviolet and visible spectrum. An alternative approach is to use an infrared, heat-sensitive array detector such as a platinum silicide or iridium silicide infrared imager. This latter choice would permit the direct monitoring of heat evolved from the probe array during a biochemical reaction such as hybridization or antibody action. DNA hybridization and other heat-generating reactions may be directly detectable through their thermal signature during reaction. The infrared transmission and reflection properties of the product (e.g., hybridized DNA) will be distinctly different than the reactants due to the formation of new molecular bonds with new absorptions from infrared-active vibrational and rotational modes in the product molecule. In the configuration of FIGS. 15 and 16, thermal properties can be monitored also by monitoring thermally generated noise in a conventional visible wavelength or IR detector array. In this case heat generated by the biochemical reaction is transmitted by thermal conduction through the thin device layers and detected as a noise burst on the electrode 220. The array may also be flood-irradiated with infrared, visible, or ultraviolet light in the configuration of FIG. 15. In this case, light is chosen specifically in a product-state (e.g., hybridized DNA) absorption band. In the unreacted state the flood illumination is transmitted through the well and reflected by filter 250. Wells in which the desired reaction has occurred become absorbing at the flood illumination wavelength. After absorption the flood illumination automatically converts to heat and is detected after conduction into the device below the active well site.

V. PROBE FORMATION

A. General

One method of forming the array 10 uses probes attached to the test sites 12 in the array. Different probes can be attached to the test sites 12 according to the type of target desired. Oligonucleotides, single or double stranded DNA or RNA, antibodies or antigen-antibody complexes, tumor cells and other test probes known to those of skill in the art may be used. The probes are attached to the test sites by fixation to a solid support substrate on the surface of the wells 42, or alternatively, attached directly to the electrodes 16 or 20, as in FIG. 4. The solid support substrates which can be used to form the surface of the wells 42 include organic or inorganic substrates, such as glass, polystyrenes, polyimides, silicon dioxide, and silicon nitride.

The solid support substrates or the electrodes must be functionalized to create a surface chemistry conducive to the formation of covalent linkages with the selected probes. As an example, a glass support can be functionalized with an epoxide group by reaction with an epoxy silane. The epoxide group on the support reacts with a 5'-amino-derivatized oligonucleotide probe to form a secondary amine linkage, as described in Parkam and Loudon, BBRC 1:1–6 (1978), which is incorporated by reference herein. Formation of this covalent linkage attaches the probes 26 to the support surface in the desired array. Examples of functionalized polystyrene surfaces include 5' aldehyde or carboxylic acid derivatives coupled to hydrazide-activated polystyrene, as described in Kremsky, et al. (1987) *Nucl. Acids Res.* 15:2891–2909, and 5' amino derivatives coupled to polystyrene which has been activated by diazotization and 5' phosphate derivatives coupled to amino-functionalized polystyrene, as described in Lund, et al. (1988) *Nucl. Acids Res.* 16:10861–10880, both articles being incorporated by reference herein.

For direct attachment of probes to the electrodes, the electrode surface must be fabricated with materials capable of forming conjugates with the probes. Materials which can be incorporated into the surface of the electrodes to provide for direct attachment of probes include electrometal materials, such as gold, niobium oxide, iridium oxide, platinum, titanium, tantalum, tungsten and other metals. These electrometals are capable of forming stable conjugates directly on the plate surface by linkages with organic thiol groups incorporated into the probe, as described in Whitesides et al. (1990) *Langmiur* 6:87–96 and Hickman et al. (1991) *J. Am. Chem. Soc.* 113:1128–1132, both of which are incorporated by reference herein. As an example, a synthetic DNA probe labeled with a thiol group at either the 5' or 3' end will form a stable conjugate with a metal, such as gold, in the plate surface to create an array of directly attached probes.

B. Array Sensitization

The probes in each test site must be uniquely capable of binding to a known molecular or cellular target. The probes may be formed (synthesized) off-chip and inserted into each test site by robotic manipulation of micropipettes. In this embodiment, the probes are linked to gold or $SiO_2$ or other materials of the test site by means of the linker chemistry described earlier. This method is sufficient to produce low density probe arrays (up to approximately 100 per centimeter).

Figure 17:
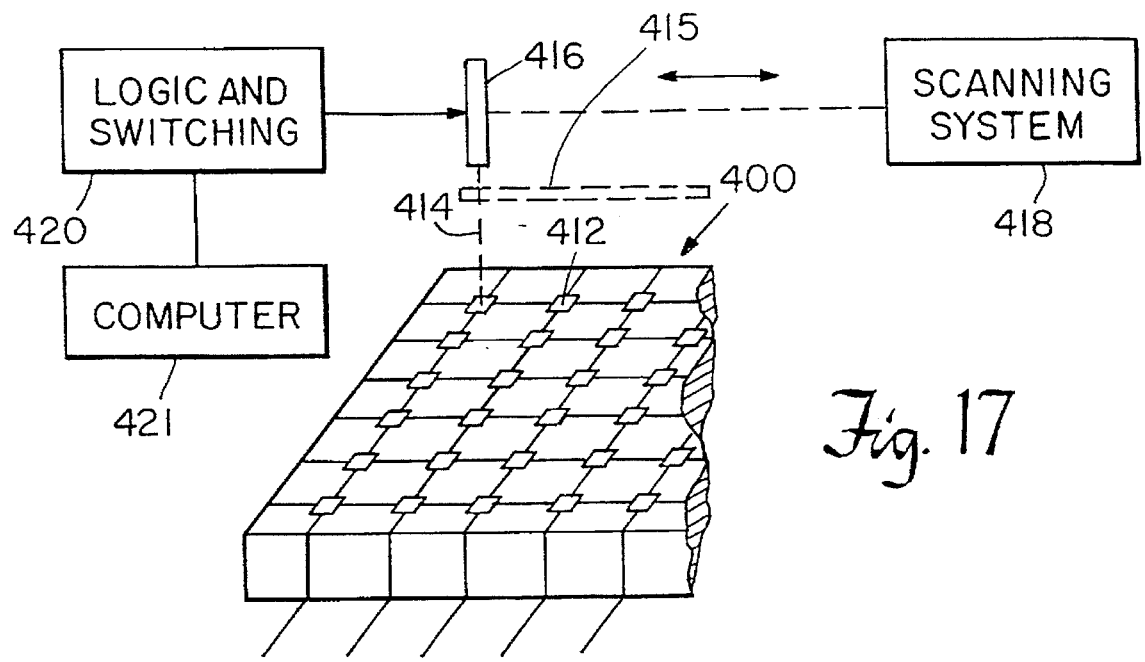
FIG. 17 is a schematic view of a system for synthesizing probes in the test sites.

Alternatively, the probes may be synthesized in each test site. This method is based upon the fact that key steps of probe synthesis are temperature dependant. By raising the temperature of a surface in a site selective manner, probe chemistry can be directed to specific test sites within an array. This approach is shown in the partial schematic of FIG. 17.

As an example of this embodiment, an array 400 of test sites 412 formed as previously shown in FIGS. 1–4. In one embodiment of this approach, probes will be synthesized upon an available $SiO_2$ surface. In order to begin probe synthesis, a linker is first attached to the surface. To achieve linker attachment, test sites are immersed in epoxysilant (fluid A), which covalently links an epoxide to the surface. The epoxide is then hydrolyzed and then blocked with trityl chloride, to protect the available primary hydroxyl.

In order to begin probe synthesis, the array is then immersed in de-protecting solution, typically dilute dichloroacetate in alcohol. Laser beam 414, generated by laser 416 is then mechanically scanned across the array by galvanometer scanning system 418. The purpose of the laser is to heat the surface at selected test sites. Operation of the beam is controlled by logic and switching circuitry 420 which is programmed to irradiate only those test sites 412 where deprotection is desired. After irradiation, the deprotecting solution is then removed, thereby revealing free OH groups at sites which were irradiated. Those test sites with free OH groups are now available to add a nucleic acid base.

DNA probe synthesis can now be performed on the array. Any of the known chemistries can be employed, including phosphoramidite, phosphotriester or hydrogen phosphonate methods. The chip is immersed in a solution containing one of the activated based precursors, adenosine (A) for example, and those test sites which had been irradiated in the previous step will link to A.

Following the standard phosphodiester chemistry, as generally employed for oligonucleotide synthesis, the chip is then re-immersed in de-protecting solution then irradiated again. For example, assume that test sites are irradiated where guanosine (G) is to be attached. After irradiation, activated G is added and the process of synthesizing a second phosphodiester bond is repeated.

The duty cycle is then performed on the chip for thymidine then cytosine. In all, because there are four nucleic acid bases, four cycles of irradiation are required to extend the probe array by one nucleic acid subunit. To synthesize an array of ten-base-long probes, forty cycles would be required.

Laser initiation of the reaction occurs either by localized heating or by photochemistry. A preferred embodiment uses a visible-wavelength or UV argon ion laser in combination with a galvanometer scanning system to initiate photochemical synthesis. Alternatively, since synthesis reactions are known to be highly temperature sensitive, an argon or infrared laser may be used to initiate synthesis by local heating of an array site.

The method can also be applied to the synthesis of peptides or other polymeric probes on solid supports, based upon the principle of thermally addressable deprotection. For example, in the case of peptide synthesis, site selective peptide synthesis is achieved by thermal removal of the f-moc protecting groups, typically in dilute base, followed by capping and the other ordinary steps of peptide synthesis.

Alternatively, a "glue" layer can be locally activated FIGS. 26A–D (or deactivated) or locally applied FIGS. 25A–D to a test site by means of scanned laser irradiation. In this embodiment the ultraviolet, visible or infrared laser is used to photochemically or thermally alter the adhesion properties of the desired array sites. The probe solution, for example of type A, is then washed over the array resulting in localized adhesion of the type A probe at the desired sites. The type A probe solution is then rapidly rinsed from the system, a second laser irradiation at new array sites is applied, and type B probe solution is introduced to adhere type B probes. The process is repeated sensitize the full array.

Array sensitization may be accomplished using, for example, a CW argon-ion or CW Nd:YAG laser using scanning optics such as galvanometers or rotating mirrors, or using a fixed laser beam with a computer-controlled X-Y stage. An activation or deactivation process in a "glue" layer can be preferably accomplished using a short-pulsed laser such as a pulsed Nd:YAG laser or excimer laser. An excellent approach is to simply cover the "glue" layer 902 to "deprotect" and thereby reveal the "glue" by ablating a passivating material 904 applied over the "glue" (See FIGS. 26A–D). Examples of "glue" layers are epoxides, thiols or hydrophilic, e.g., hydrated surfaces. Passivating materials can be hydrophobic materials such as fluorine-terminated fluorocarbons or the derivatives or hexamethyldisilizane.

FIGS. 25A–D and 26A–D illustrate two alternate methods of probe formation using the "glue" approach. Furthermore each show two alternate ways to activate a test site. One way is to use a programmable element such as a heater element 906 embedded beneath a test site to induce a thermal reaction in the test site and thereby create or deposit a glue layer 920 to which the probes adhere. Fully synthesized probes 912 are washed over the cite and adhere to the exposed glue layer site 920, FIG. 25D. Next another site is formed or exposed and a different probe attached. Alternatively external radiation as in FIG. 25B is used to form the glue layer 920; or as in FIGS. 26B and C to ablate a passivating layer 904 and expose a glue layer 902.

In addition to the use of a scanned laser beam, an alternative "direct patterning" method may be employed using a stationary illumination beam with a reconfigurable "light-valve" 415 (shown in dotted lines in FIG. 17) such as a liquid-crystal display or switchable mirror array, which is illuminated with a laser or intense lamp. The illuminated "light-valve" is imaged onto the sensor array, 400, with a lens system (not shown). The pixel elements in the "light-valve" are electronically switched "on" or "off" to select corresponding areas to be sensitized in the sensor array, an excellent "light-valve" device for this purpose is described by J. A. Neff et al. (Proc. of the IEEE, Vol. 78, No. 5, May 1990).

Another approach to on-chip synthesis of probes is described in PCT International Publication Number WO 90/15070, entitled "Very Large Scale Immobilized Peptide Synthesis" to Pirrung et al., assigned to Affymax Technologies, having an International Publication Date of Dec. 13, 1990, which is incorporated by reference herein. This approach is based upon laser directed photochemistry of protecting groups, rather than site directed thermal chemistry or surfaces.

Another method for synthesizing probe strands uses the embedded resistors 32 described in connection with FIGS. 1 and 4 to locally heat predetermined array test sites without substantially heating adjacent sites. This would enable thermally activated synthesis of probes, such as short oligonucleotide strands, to take place in situ in response to application of voltages across selected resistors. Alternatively, high currents would be applied to heat all resistors, except those adjacent to wells where a reaction is desired. In this alternative, the non-synthesized wells are kept at a temperature above the desired synthesis temperature, thereby preventing a synthesis reaction from taking place in these wells.

The electrically addressable test site array of the invention also provides the ability to electronically induce or catalyze a synthesis reaction in a given well, or row, or column of wells, by applying an electrical potential to the electrodes of such well or wells.

The potential can be used to attract chemical reactants from solutions disposed near the wells and/or to catalyze a specific chemical reaction in the wells.

Furthermore, the hybridization between target molecular structures and completed probes can be enhanced by the application of an electrical potential to the electrodes just after the target solution is applied to the test sites. Without the application of a potential, the target molecular structures must diffuse through the solution to the probes. Due to the inefficiency of such a diffusion process, one must allow typically 1.5 to 2 hours for significant hybridization to take place, and even then a substantial number of probes remain unhybridized. An electrical potential can draw charged target structures directly to probes near to or attached to the electrodes, increasing both the rate of hybridization and the total number of target/probe hybridizations that can be conveniently produced in a given experiment. Conversely, a reverse biased potential can be subsequently applied to aid in the washing (removal) of unhybridized and mismatched target molecules. This technique is not only applicable to the electronic genosensors of FIGS. 1 through 9, which have electrodes present within each test site, but can be employed in both the micromechanical-resonator and CCD-based approaches by either using the electrodes present within or under each test site or fabricating one or more additional electrodes at each test site for this purpose.

Alternatively, the potential applied to individual wells can be used to draw a current surge through the well structure sufficient to evaporate a "glue" layer or glue passivating layer similar to that described above in the last method. Sensitization of the array is similar to the electronic programming of an array of electrical fuses.

Figure 18:
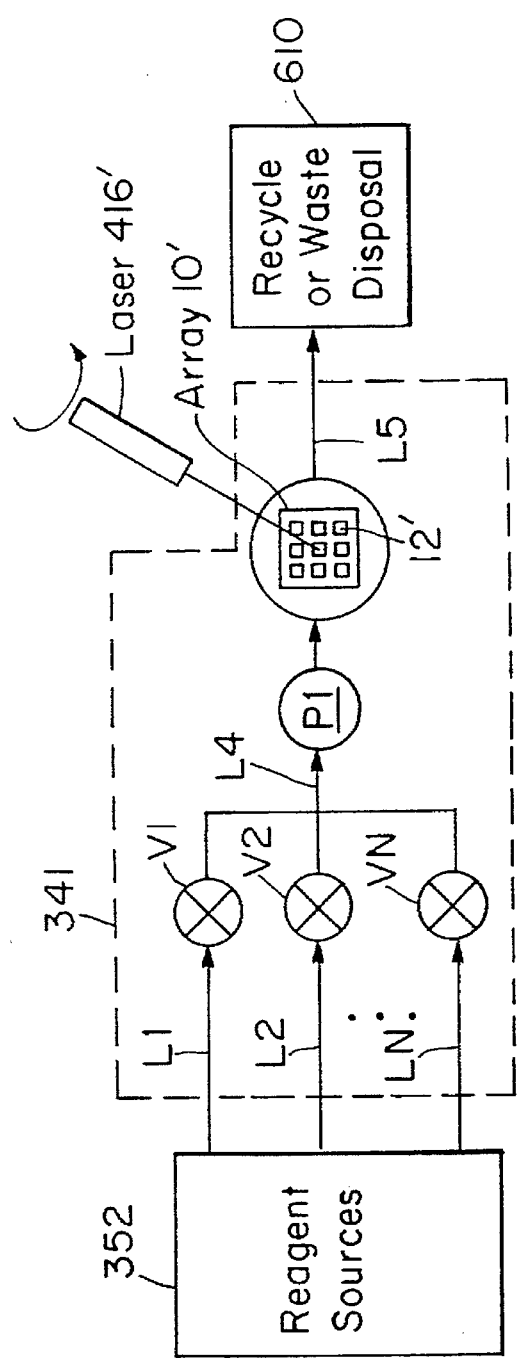
FIG. 18 is a schematic illustration of a microfluidic system for synthesizing probes in situ.
Figure 19:
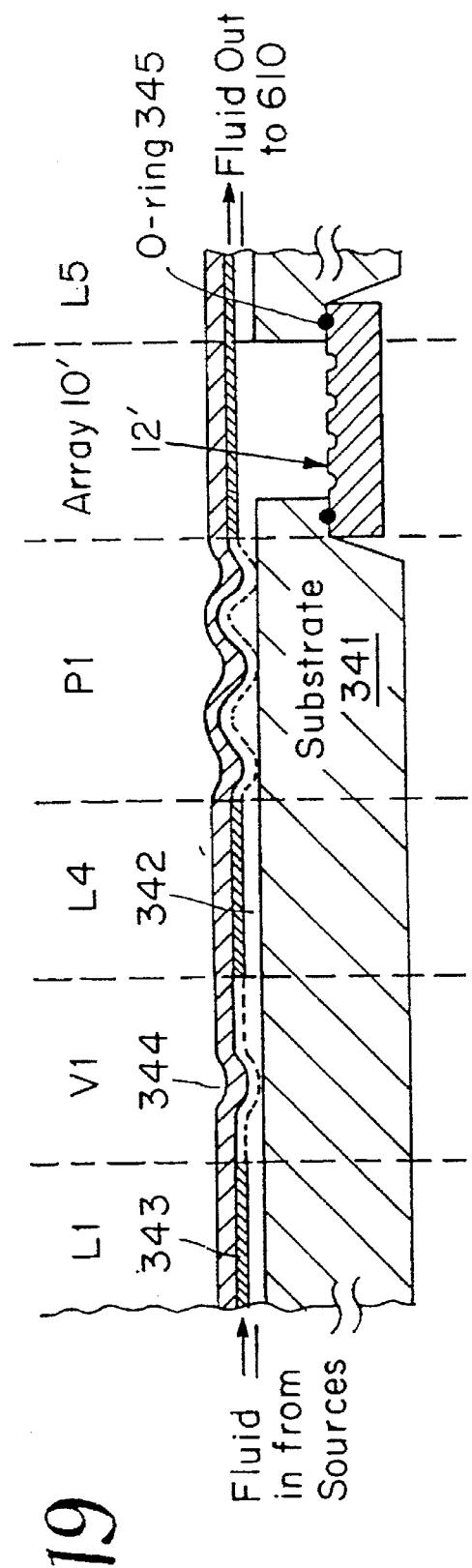
FIG. 19 is a schematic cross-section of the microfluidic system of FIG. 18.

Referring now to FIGS. 18 and 19, a microfluidic system for synthesizing unique genosensor probes in situ in a test site will now be described. In this embodiment, reagent sources 352 are individually fluidly coupled via channels L1, L2 - - - LN to respective microchannel valves V1,V2 - - - VN formed in a suitable substrate 341. Valves V1–VN enable flow of solution into manifold line L4. Microfluidic peristaltic pump P1 forces the solution onto array 10', which is enclosed by laser-radiation-permeable films 344 and 343, such as silicon nitride or silicon dioxide.

Radiation from laser 416' is selectively projected onto individual test sites 12' formed in substrate 341, in accordance with previously described scanning or imaging methods. Laser scanning of test sites induces localized activation of individual sites as the input solution fluids are rapidly switched using valves V1–VN.

The entire fluidic system as well as the array may be formed on a single chip of semiconductor or dielectric material, such as Si, glass, $Al_2O_3$, etc. Channels 342 are etched into the substrate 341 using conventional photolithography and etchants or by micromachining techniques. An array 10' of test sites 12' is formed in the substrate, as described in connection with FIGS. 1–6.

The microfluidic flow system depicted in FIG. 19 can be formed as follows. A photoresist material is spin-coated on a substrate 341, formed, for example of pyrex glass. The microchannel structure is then patterned into the photoresist using standard photolithography and the pattern, including channel structures 343 and 342, are transferred into the substrate by etching using buffered HF. A membrane actuator layer 344, comprised of preferably a piezoelectric, such as lead zirconium titanate or PVDF polymer and metal electrodes, is then bonded to the microchannel structure. During sensitization the array 10' is sealed against the microfluidic system preferably using an elastomer O-ring 345. Alternate membrane actuator layers, known to specialists in the art, make use of shaped memory alloys rather than piezoelectrics, or are based on passive materials deformed electrostatically, for example, aluminum films which are deflected by DC voltages applied to electrodes (not shown).

Mass production of the flow channel structure is feasible using the photolithographic techniques above. For certain channel shapes it is preferable to use laser micromachining techniques, such as those developed for etching of silicon in a chlorine ambient. Using either photolithography or micromachining a negative-form mold can be made then replicated in positive form, for example, using thermocompression methods.

VI. Microfluidic Molecular Detection

Figure 20:
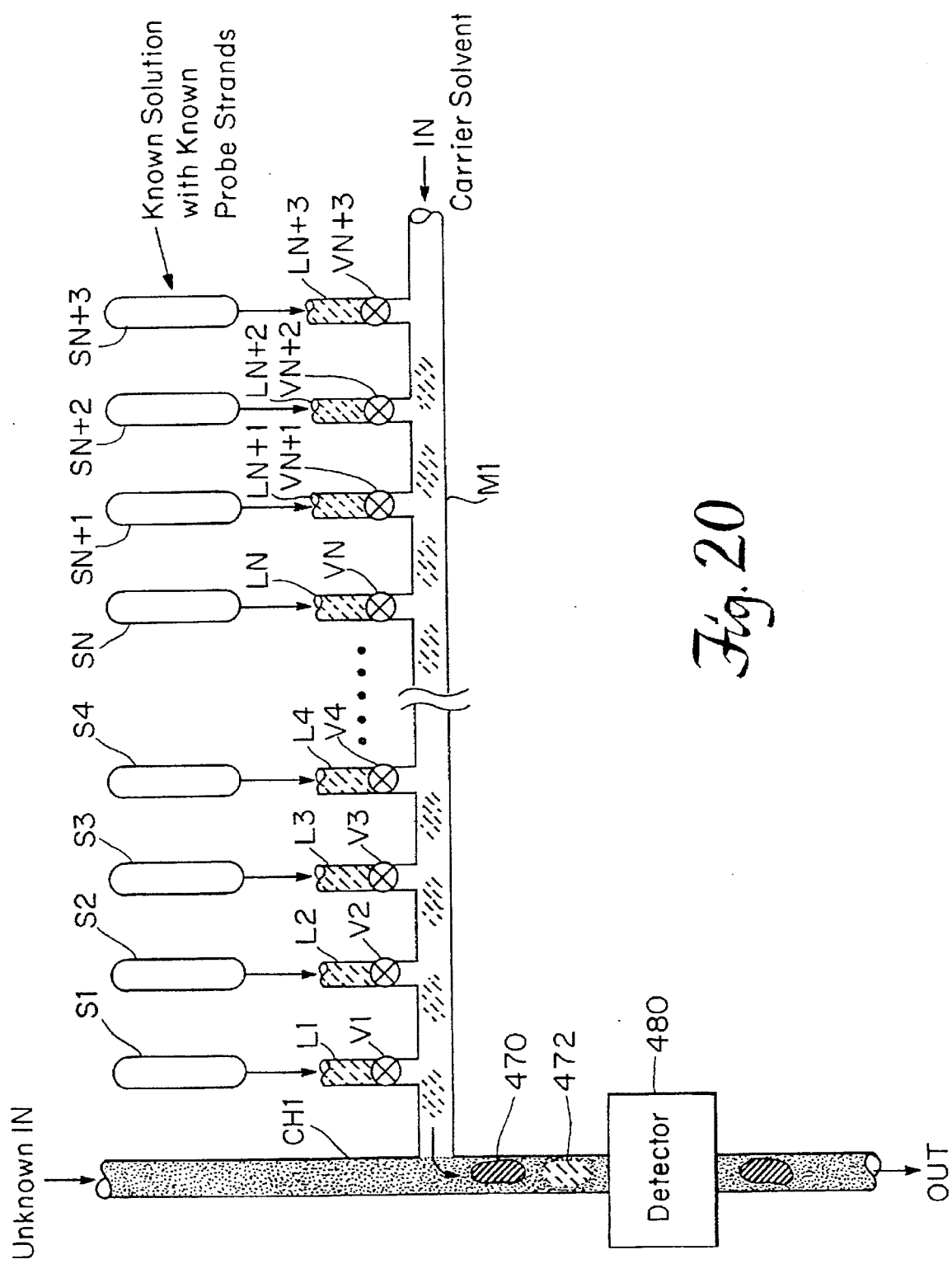
FIG. 20 is a schematic of a microfluidic genosensor embodiment.

The arrays discussed above operate on the principle of massively parallel templating. An alternative approach is illustrated in FIG. 20. This system is a fast serial microfluidic detector that operates with nanoliter or picoliter solution volumes. This system is composed of a microfabricated system of capillary channels and valves V1–VN+3 connected to a main channel C1 and a single (or several ganged) high sensitivity detector array(s) 480 formed as previously described. A steady but low-volume stream of a solution containing unknown molecules is mixed using the methods described above in connection with FIGS. 18 and 19. The unknown solution is sequentially mixed with similarly small volumes of a solution containing known unique batches of oligonucleotide strands from sources S1–SN+3 in a fluidic flow. The detector 480 monitors the flow to assess which oligonucleotide batches have reacted with the unknown molecules in a hybridization reaction. Hybridization can be detected, as previously described, either electrically or optically by observing a characteristic shift or distinct spectral feature in the electrical or optical properties of the solution as it flows past the detector. An important feature of this system of FIGS. 20, 18 and 19 is the use of an extensive channel or capillary network that has minimal dead volumes and fast fluid velocities to allow sequential processing of the flow without diffusion-induced smearing of the batches. This concept is impractical using macroscopic tubing and valves, hence it is preferred to miniaturize such a network. In recent experiments, we have demonstrated laser microchemical milling of 1- to 10-µm-diameter flow channels in silicon using the methods described above in connection with FIG. 19. Inexpensive replication of a micromachined network that exists on a Si wafer might be accomplished by injection molding or embossing. The valves require integrated electrical actuators which may be switched by either an on-board or off-board microprocessor.

VII. Probe Bonding Mechanism

Figure 21:
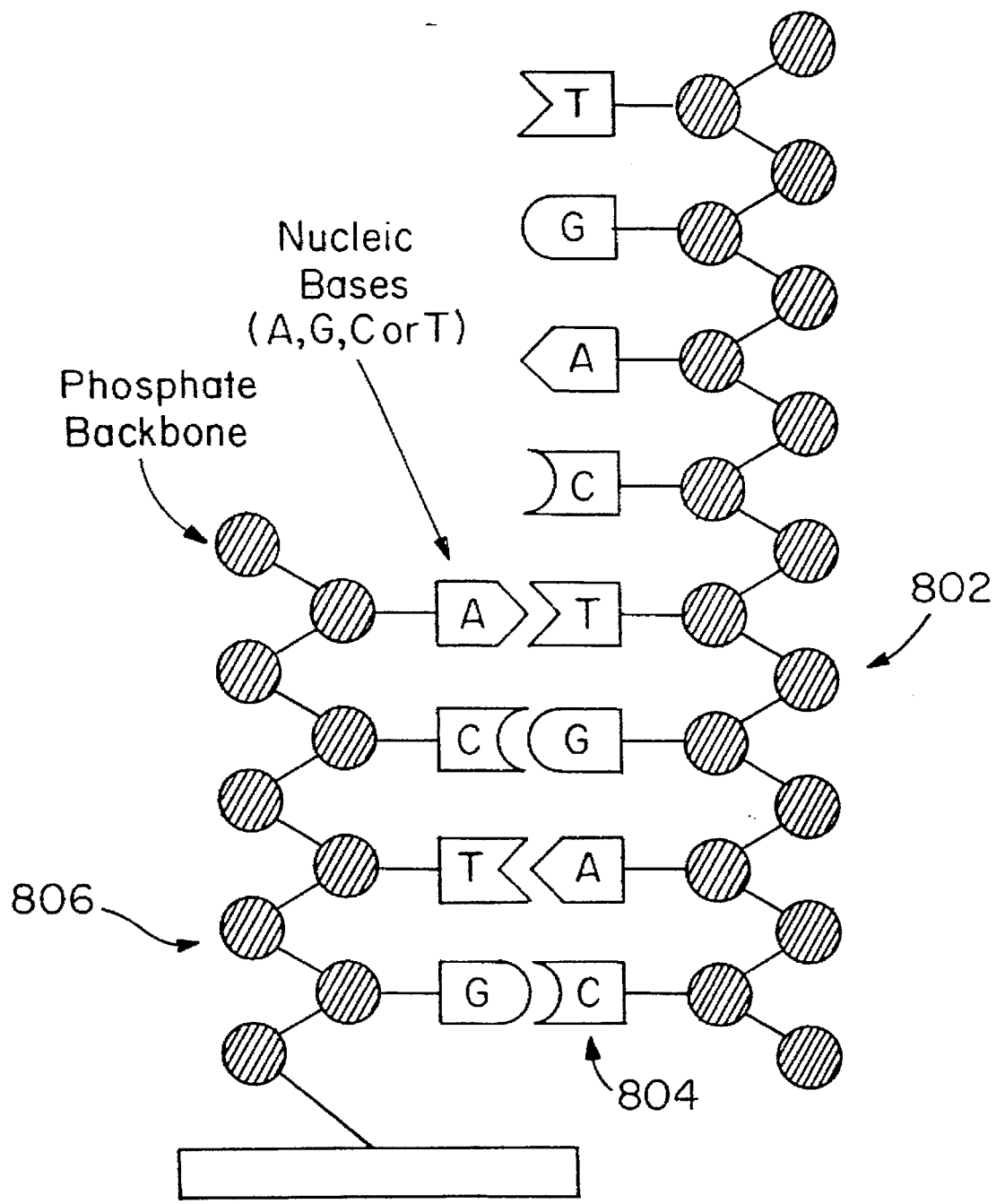
FIG. 21 is a schematic illustration of the method whereby a synthetic DNA probe selectively binds to a predetermined DNA sequence.

A schematic illustration of the bonding mechanism for sequencing using a synthetic DNA probe is shown in FIG. 21. Sequencing by hybridization (SbH) is a new sequencing approach which exploits the natural base pairing property to provide a recognition mechanism for decoding the nitrogenous bases comprising DNA. In FIG. 21 a partial sequence 802 of a DNA sample is represented on the right. Four bases 804 in the sample DNA are specifically paired with a short piece of synthetic DNA 806 attached to a surface. The support-bound DNA "probe" serves as a recognition element for the occurrence of a perfectly complementary sequence in the sample "target" DNA 802.

The concept of using a larger set of DNA probes to decipher the base sequence of a DNA sample target is illustrated below. Example I shows a small portion of the base sequence of a DNA sample, which has been converted to single-stranded form by heating prior to analysis. By exposing the sample DNA to a set of synthetic DNA probes representing all possible sequences for a given probe length (for example, all 65,536 8-base probes), and then detecting which probes have specifically bound to the target DNA, a complete list of oligonucleotide sequences contained in the DNA sample can be generated. In the case shown in Example 2 (below) only those 8mer probes listed would hybridize to the sample DNA sequence. In turn, an overlapping algorithm is used to generate the complete sequence of the target DNA from the oligonucleotide content.

EXAMPLE I

Unknown Single Strand DNA (Target)

ATCGCTTACGGTAATC                  (SEQ ID NO:1)

EXAMPLE II

Hybridized Synthetic Genetic Probes

TAGCGAAT
AGCGAATG
GCGAATGC
CGAATGCC
GAATGCCA
AATGCCAT
ATGCCATT
TGCCATTA
GCCATTAC

VIII. APPLICATIONS

Commercial applications of the present invention with regard to DNA and RNA detection include genetic research, genetic and infectious disease diagnosis, toxicology testing, individual identification, agriculture identification and breed optimization, quality assurance through contaminant detection, and occupational hazard screening via mutation detection.

There are currently estimated to be 4,000 to 5,000 genetic diseases in humans, in which a mutational change in a gene destroys or hinders the function of a gene product, leading to a serious medical condition. The affected genes and proteins (gene products), have thus far been identified for a small fraction of human genetic diseases, although the number is increasing steadily. A few examples of human genetic diseases for which mutations associated with the disease have been identified include cystic fibrosis, phenylketonuria, Alzheimers' disease, cancer, Duchenne muscular dystrophy, and familial hypercholesterolemia. Although, in some cases, the disease is associated with one or very few specific mutations, it is becoming evident that many, if not most, genetic diseases can be caused by any of numerous mutations, scattered along the affected gene. In the former case, the presence of a defective gene can be detected through the use of simple DNA hybridization detection tests in which a synthetic DNA probe is used to discriminate between a wild type and mutant DNA sequence. In the latter case, a substantial DNA sequencing effort is required to search through an entire gene for mutations that may be associated with a disease.

The importance of detecting mutations within disease-linked genes lies in both the ability to screen for carriers of recessive genetic diseases, leading to genetic counseling and informed reproductive decisions, and the means for making prenatal diagnoses which can enable therapeutic intervention. By appropriate choice of oligonucleotide probes, the sequencer 10 leads to a new gene-targeted DNA sequencing procedure which rapidly detects any mutation within a target gene, facilitating the diagnosis of genetic diseases and identification of carriers, especially when a variety of different mutations may cause the defect. Perhaps even more important is the rapid, high throughput nature of the procedure which promises to facilitate population studies aimed at discovering which mutations within a target gene are actually associated with a disease and which mutations represent harmless polymorphisms. This information is expected to lead to simplification of the technology for specific detection of disruptive mutations, and valuable structure-function relationships that facilitate the development of therapeutics.

The present invention is not limited to genetic diseases; it may be used for rapid, high throughput identification of infectious agents. Each species or strain of a virus or micro-organism is predicted to yield a unique, diagnostic pattern of hybridization within an array 10.

The gene-targeted mutation detection described above will also have important uses in environmental research, for example, the detection of mutations induced by chronic exposure of cells to chemical agents. Similarly, the present invention may be used for individual monitoring of employees who may be exposed to chemicals or radiation in the workplace (e.g., through periodic screening for mutations in populations of circulating lymphocytes). An important application of this technology will be the development of a predictive model of mutagenic risk via the characterization of large scale and point mutations in specific genes, such as that for hypoxanthine-quanine phosphoribosyl-transferase (HPRT).

High density arrays will find numerous uses in genome sequencing, and will likely play an important role in the current Human Genome Project (HGP) effort to determine the entire sequence of 3 billion base pairs in the human genome. More importantly, however, are the new human genome projects that will arise because of the availability of fast, high throughput sequencing technology. There will be a need to conduct repetitive DNA sequence analysis of important parts of the human genome derived from large numbers of individuals, in order to characterize complex multi-gene disease conditions and other genetic traits. This activity will persist long after the current HGP is completed and will bring revolutionary progress in biomedical sciences.

Another potential use of the present invention is in "DNA typing", in which DNA sequence differences between individuals are analyzed. The sequencer of the present invention for simultaneously screening large numbers of polymorphic markers in the DNA of an individual has tremendous advantages over the current technique of restriction fragment length polymorphism (RFLP) analysis, which is time consuming and laborious. DNA typing can play an important role in forensics and paternity testing. In addition, there is interest in DNA typing all personnel in the armed services.

As valuable new plants and livestock are developed by genetic engineering, there will be a need for DNA typing to verify the source and ownership of agricultural products. The sequence information that will come from genome sequencing in humans, plants and animals will lead to increased application of genetic engineering techniques to develop pharmaceutical agents and create improved crops and livestock. Examples include strains that are more resistant to disease and harsh climates, as well as crops that have a greater yield or higher nutritive value.

The present invention can be used in connection with detection of targets which are molecular structures other than DNA or RNA, such as cells and antibodies. Table III sets forth feasible probe types for other molecular structures serving as targets. The stated probe types are not meant to be exclusive.

TABLE III

| | Probe Types | |
|---|---|---|
| Target | | Probe |
| DNA, RNA | | Oligonucleotide |
| Antibody | | Antigen (peptide), anti-antibody |
| Cell | | Antibody, protein |
| Hormone receptor | | Hormone |
| Aviden | | Biotin |
| Immunoglobulin | | Protein A |
| Enzyme | | Enzyme Factor |
| Lectins | | Specific Carbohydrate |

Figure 22:
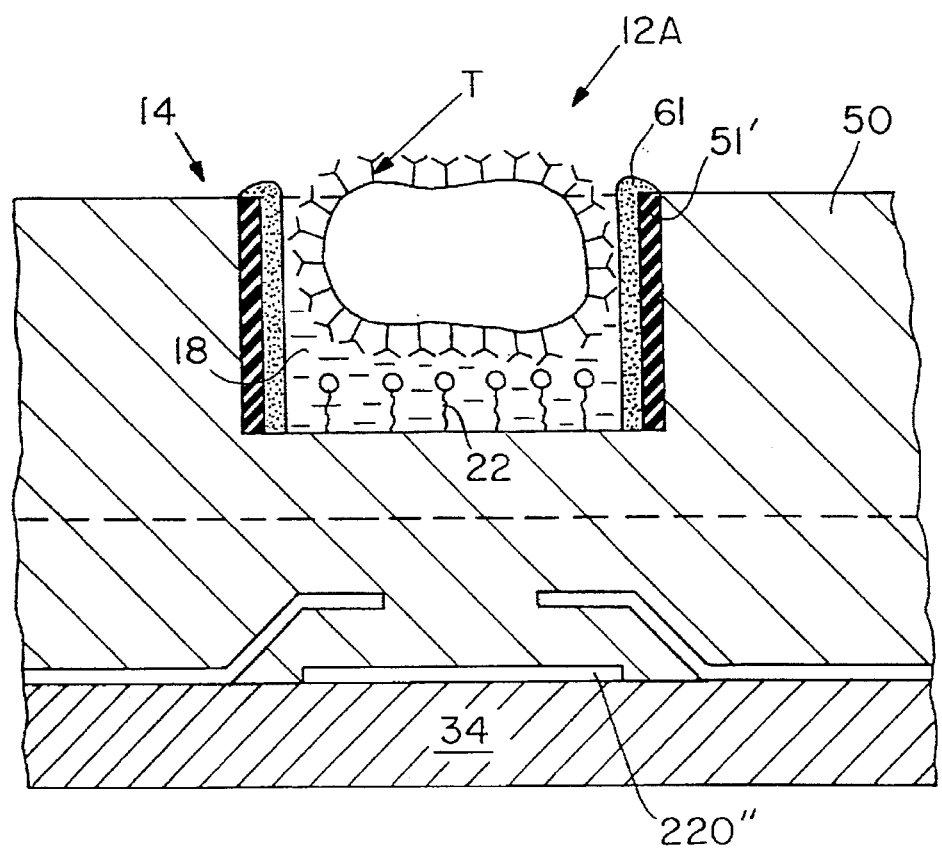
FIG. 22 is a schematic cross-section of a test well used to detect molecules in biological fluids.

When the detector employs peptides or other antigens as probes, it can be used to detect antibodies in biological fluids, as shown in FIG. 22.

In this embodiment, a peptide antigen (the probe 22) is affixed to the $SiO_2$ 50 at the bottom of the test well 12A (similar to that illustrated in FIG. 6H), employing a bifunctional crosslinker such as one with a silane at one end and an epoxide or other peptide specific group at the other.

The treated surface is then incubated with a fluid 18 containing antibody (the target T). Because antibodies are large macromolecules (150,000 to 950,000 MW, depending on class), the resulting target/probe bonding produces a large change in the permittivity of the test well 12A. The magnitude of the effect can be additionally amplified by treating the target/probe complex with a second antibody which is specific for the target antibody, thereby creating a very large complex.

The affinity and selectivity of antibody/antigen and antibody-antibody interaction are well known and are the basis for an existing class of biotechnology (ELISA assays, immunohistochemistry, and others). The technology described here employs those well understood binding interactions in a new microelectronic detection scheme.

The commercial application of the methodology is for use to detect the presence of any of hundreds of thousands of different antibodies or other proteins, simultaneously, in a blood sample or other biological fluid. This is particularly useful in blood typing, the detection of viral infection such as AIDS, or the diagnosis of cancer. It would also be very useful as a research tool. It would replace or augment the use of ELISA assays and other biochemical methods to detect antibody/antigen interaction.

When the detector employs as a probe, peptides, antibodies or other molecules which bind to cells, it can be used to detect specific cell types in biological fluids.

In this embodiment, the probe 22 comprises an antibody, protein or other molecule which is known to bind to the cell surface. The target T in this case is an intact cell having receptors T for bonding with the probes 22.

A fluid solution containing cells is added to the detector. Subsequent to the target/probe binding interaction, binding gives rise to detector wells which are coupled to a cell. Since cells do not conduct current and display low frequency dielectric relaxation, binding of a cell can be detected by either a change in absolute conduction in a well (a modification of the Coulter principle) or by the induction of a low frequency dielectric relaxation effect.

The commercial application of the methodology is for use to detect the presence of cells with altered cell surface properties, especially cells in the blood or other bodily fluids. Cells from solid tissues could be analyzed subsequent to standard tissue dispersement methods. Such a detector would be useful in the diagnosis of viral infection and for cancer diagnosis, as well as a scientific research tool. It would serve as a replacement for the use of fluorescence microscopy (immunohistochemistry) and fluorescence activated cell sorting.

IX. ADVANTAGES

Current microfabrication techniques enable inexpensive construction of multimegabit memories that exhibit uniform densities and properties. Hence arrays containing potentially millions of individual biological test wells or sites can be miniaturized comparable to standard electronic devices at a similar cost. For example, a 1 cm by 1 cm array could easily be fabricated containing one million biological test sites. Moreover, the uniform electrical properties of the devices fabricated in such manner enhance the detection sensitivity beyond many other approaches.

One important advantage of the microfabricated electronic detector and the optical-absorption CCD detector described previously is that the detection method provides direct detection of target/probe molecular binding. Hence no toxic fluorescent, radioactive, or chemical marker need be attached to the targets or probes. Rather, only an appropriate electrical signal or frequency shift must be experienced for detection. Such signals or shifts naturally occur for many target/probe combinations, such as DNA and RNA to an oligonucleotide. However, if the signal or shift in the electronic detector is weak or nonexistent after bonding, a charged molecular marker can be attached to the target. In addition, detection in the electronic detector is observed by a change in frequency characteristics, as opposed to a change in magnitude characteristics which can be obscured in time as the microfabricated array is exposed to the corrosive biological solutions. Thus, the device may be cleaned and reused a number of times without affecting its accuracy. Although the method of detection will withstand some corrosion of the electrodes, a passivation layer can be employed to coat the plates for even longer use.

Another advantage of the present invention is that the electronic circuitry used to interrogate the test sites to perform the detection measurements can be fabricated directly on the wafer containing the biological array. Switch matrices, signal processing circuitry, and energy sources could all be incorporated on the same chip to facilitate rapid detection across the array. Consequently, the incorporation of active circuitry on the wafer would also greatly reduce the cost of experimentation.

The density of the probes 22 attached at the test site 12 directly determines the sensitivity. The microelectronic method has been shown to provide a factor of ten discrimination between short (nonhybridized) and long (hybridized) single-stranded DNA fragments, whereas the intercalating-dye optical approach provides a factor of three.

The elimination in most embodiments of radiographic film reduces the testing time since film exposure is not required. Sample preparation time is reduced greatly since the nucleic acid fragments need not be labeled. The detection method is quick; the measurements can be performed as soon as sufficient molecular binding is completed. Furthermore, the measurement process can be automated via on-chip microprocessor control to provide a very fast method of accessing each test site in the array.

The microelectronic technology incorporated into these types of detection devices will drastically reduce the price for such experimentation. Essentially, the efficient mass production techniques employed in making megabit memory chips and megapixel CCD imaging chips can be employed.

Although the present invention and its advantages have been described in detail, it should be understood that various changes, substitutions and alterations can be made herein without departing from the spirit and scope of the invention as defined by the appended claims.

Figure 24:
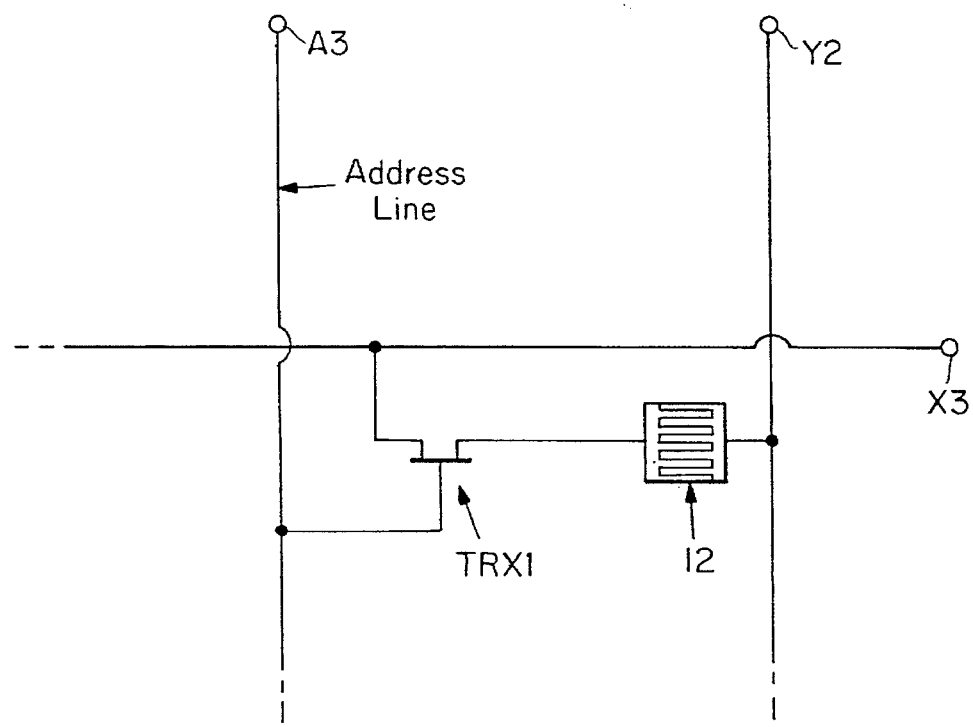
FIG. 24 is a partial schematic of an alternative addressing embodiment of the invention.

For example, the active circuitry of the genosensor array, such as circuits 36, 56, 38, 58 and 40 of FIG. 1, can be integrated monolithically with the array of wells or the same substrate. Switch matrices, analog testing circuits, and analog or digital (microprocessor) controllers could all be fabricated on the same wafer to perform or simplify the electrical tests. As shown in FIG. 24, transistors, such as, TRX 1, could be integrated into each substrate adjacent to a respective test site 12, for example, to disconnect each site electrically, except when it is being sampled. This would necessitate an additional address line A3 for each column but would reduce parasitic capacitance and spurious signals from lines not in use. A greater reduction of these undesired effects could be achieved by a second address line and set of transistors coupled to the Y-side of the site 12.

CCD circuitry (including CCD implementations of neural networks) has been demonstrated that can perform a wide variety of signal processing and pattern recognition functions. Integration of a CCD dataprocessing circuit with a genosensor array could simplify the DNA detection and decoding, and would be compatible with the integrated CCD imager, as described in connection with FIGS. 15 and 16.

While the invention has been illustrated in connection with a wet type of testing in which solutions are used; it is entirely feasible to use a "dry" or "gel" approach in which the probes and hybridized probe/target combinations are formed in a dry medium or in a gel.

We claim:

1. A method for testing a sample substance for the presence of target nucleic acids comprising the steps of:
    a) forming an array of test sites in multiple locations, each site having oligonucleotide probes formed therein of known binding characteristics and wherein the probes in each test site differ from the probes in other test sites in a known predetermined manner, such that the test site location of probes and their binding characteristics are also known;
    b) applying the sample substance to the test sites; and
    c) detecting a change in the electromagnetic properties of the test sites resulting from the binding of target nucleic acid within the sample substance to probes in the test sites by detection circuitry coupled to individual test sites to determine which target nucleic acid have bonded to a test site; whereby the presence of a multiplicity of different target nucleic acids in the sample can be detected.

2. The method of claim 1 wherein a test signal is applied to the test sites which is an electro-magnetic signal and forming said array comprises the steps of:
    a) forming a first layer on a substrate;
    b) forming a second layer on the first layer;
    c) forming openings in the second layer into the first layer exposing a portion of the first layer; and
    d) forming a pair of electrodes, one electrode on the first layer on the exposed portions in the openings and another electrode on the second layer adjacent to the openings, and wherein said test signal is applied to the electrodes.

3. The method of claim 2 wherein forming said pair of electrodes comprises the steps of depositing metallization on the second layer after the openings are formed; which metallization forms an upper electrode on the surface of the second layer between openings and a lower electrode on the exposed portions of the first layer.

4. The method of claim 3 wherein the substrate is formed of silicon, and the first layer and second layer are formed of a silicon based dielectric.

5. The method of claim 4 wherein the first and second layers are $SiO_2$ and $Si_3N_4$, respectively, and the metallization comprises Al, Ti, Pt, W, Ta and their silicides or Au.

6. The method of claim 1 wherein said step of detecting comprises detecting the dielectric properties of the test site.

7. The method of claim 1 wherein a test signal is applied to the test sites which is a pulsed or varying frequency signal.

8. The method of clam 1 wherein each test site is formed with a resonant structure which is resonant in a frequency range of electrical signals.

9. The method of claim 8 wherein said detecting step comprises detecting changes in the Q or the resonant frequency of the resonant structure.

10. The method of claim 1 wherein said sample substance is in a solution or a gel.

11. Apparatus for synthesizing molecular probes in situ comprising:
    a) an array of test sites each site containing precursor molecules to be reacted;
    b) an array of resistors disposed adjacent to the test site array with a respective resistor located in proximity to a respective test site; and
    c) coupling means for coupling a respective resistor to an electrical source for heating a respective resistor to induce a thermal reaction for synthesis of molecules in a respective test site.

12. The apparatus of claim 11 wherein the test site array and resistor array are formed as an integrated structure.

13. Apparatus for synthesizing molecular structures in situ comprising:
    a) an array of test sites each site containing precursor molecules to be reacted; and
    b) each test site containing electrodes coupled to a voltage source for inducing a reaction to synthesize molecules in a respective test site.

14. The apparatus of claim 13 wherein the array and electrodes are formed in integrated structures.

15. A method for synthesizing a plurality of different known molecular structures on an array of test sites comprising:
    a) providing an array of test sites;
    b) providing a source of chemical reactants disposed adjacent the test sites;
    c) providing electrodes associated with respective test sites; and
    d) applying a potential to a respective electrode to synthesize said different known molecular structures at said different known sites in the array.

16. Apparatus for enhancing hybridization between a synthesized probe and a target molecule comprising:
    a) an array of test sites each site containing a plurality of probes, each test site having probes of known binding characteristics, and wherein the probes in each test site differ from the probes in other test sites in a known predetermined manner;

b) an electrode associated with each site;

c) a source of target molecules applied to said sites; and d) a voltage source for applying a potential to a respective electrode for attracting said target molecules to said probes.

17. The method of claim 6 wherein the dielectric property is permittivity.

18. The method of claim 1 wherein the sample substance is in a solid state.

19. The method of claim 8 wherein the resonant structure is a transmission line and changes in phase or amplitude of a signal propagated on the line are detected.

20. A method for determining the presence of molecular structures within a sample substance comprising:

a) forming an array of test sites having specific known oligonucleotide probes formed therein selected to bind with said structures of known binding characteristics, each site having oligonucleotide probes which bind to a different structure and wherein the location of the sites containing specific known oligonucleotide probes is also known;

b) dispensing a sample substance into a test site;

c) generating radiation through the test sites; and d) detecting, by detection circuitry coupled to individual test sites of the array, the difference in the radiation which is absorbed by the respective test sites to determine the presence of the structures which are bonded to a probe.

21. The method of claim 20 wherein the difference is detected by an array of detectors formed of charge-coupled devices which are optically coupled to the test sites of the array.

22. The method of claim 20 wherein the difference is detected by an array of detectors formed integral with the array of test sites.

23. The method of claim 20 wherein the difference is detected by an array of detectors formed separate from the array of test sites.

24. The method of claim 23 wherein the array of detectors is aligned with the array of test sites and radiation is projected through the test sites onto the detector array.

25. The method of claim 24 wherein the radiation is in the form of photons, or radioactive particles.

26. The method of claim 20 wherein the radiation is generated within the test sites by a radioactive, chemical, thermal, chemiluminescent, or luminescent reaction.

27. The method of claim 20 wherein the detectors detect thermal energy occurring when a bonding reaction takes place.

28. A method for attaching probes to a test site formed in a substrate comprising the steps of:

a) forming test sites in a substrate;

b) forming an adhesive material in the test site which material enables probes to attach to the test sites;

c) forming a coating over the adhesive material;

d) contacting the coating with a coating-removal material while selectively initiating a reaction at a selected site which removes the coating at the selected site; and e) contacting the site in which the coating has been removed with probes which adhere to the adhesive material.

29. The method of claim 28 wherein the probes are presynthesized and the test sites consist of wells, the adhesive material is an epoxide, the coating is formed by hydrolyzing the epoxide, the coating-removal material is an acetate alcohol solution and the reaction is initiated at a selected site by heating the site.

30. The method of claim 28 wherein the reaction is initiated by selectively energizing resistors formed adjacent the test sites to heat the selected test sites.

31. The method of claim 30 wherein non-selected test sites are maintained at a temperature above the desired reaction temperature.

32. The method of claim 28 wherein the reaction is initiated by irradiating selected sites with light.

33. The method of claim 32 wherein the light is in the visible or ultraviolet wavelength range and a photochemical reaction occurs.

34. The method of claim 32 wherein the light originates from a laser which is scanned from site to site to initiate the reaction.

35. The method of claim 32 wherein the light induces local heating of the site to initiate a reaction.

36. The method of claim 32 wherein the light is generated by a light valve which projects light onto selected sites.

37. The method of claim 32 wherein the light source is a light valve for projecting light onto selected sites.

38. The apparatus of claim 13 wherein the voltage source provides a reverse biased potential applied to the electrodes subsequent to molecule synthesis.

39. The apparatus of claim 16 wherein the voltage source provides a reverse biased potential applied to the electrodes to aid in the removal of unhybridized target molecules.

* * * * *